United States Patent
Tsukada et al.

(10) Patent No.: US 7,549,746 B2
(45) Date of Patent: Jun. 23, 2009

(54) FUNDUS OBSERVATION DEVICE

(75) Inventors: Hisashi Tsukada, Tokyo (JP); Hiroaki Okada, Tokyo (JP); Yutaka Nishio, Tokyo (JP); Yasufumi Fukuma, Tokyo (JP)

(73) Assignee: Kabushiki Kaisha Topcon, Tokyo (JP)

( * ) Notice: Subject to any disclaimer, the term of this patent is extended or adjusted under 35 U.S.C. 154(b) by 0 days.

(21) Appl. No.: 11/689,141

(22) Filed: Mar. 21, 2007

(65) Prior Publication Data

US 2007/0222945 A1  Sep. 27, 2007

(30) Foreign Application Priority Data

Mar. 24, 2006  (JP)  ............... 2006-082124

(51) Int. Cl.
*A61B 3/14*  (2006.01)
(52) U.S. Cl. ...................... 351/206; 351/210
(58) Field of Classification Search ......... 351/205–206, 351/221; 354/64
See application file for complete search history.

(56) References Cited

U.S. PATENT DOCUMENTS

| | | | |
|---|---|---|---|
| 5,120,122 A * | 6/1992 | McAdams | 351/206 |
| 5,459,570 A | 10/1995 | Swanson et al. | |
| 5,537,162 A | 7/1996 | Hellmuth et al. | |
| 6,004,314 A | 12/1999 | Wei et al. | |
| 6,826,359 B1 | 11/2004 | Takeda | |
| 2004/0036838 A1 | 2/2004 | Podoleanu et al. | |
| 2007/0030450 A1* | 2/2007 | Liang et al. | 351/206 |
| 2007/0159597 A1* | 7/2007 | Fukuma et al. | 351/206 |
| 2007/0188707 A1* | 8/2007 | Nanjo | 351/206 |

FOREIGN PATENT DOCUMENTS

| | | |
|---|---|---|
| JP | HEI 05-095906 | 4/1993 |
| JP | HEI 11-004808 | 1/1999 |
| JP | 2003-000543 | 1/2003 |
| JP | 2004-350849 | 12/2004 |
| JP | 2005-241464 | 9/2005 |

OTHER PUBLICATIONS

Extended European Search Report.

* cited by examiner

*Primary Examiner*—Scott J Sugarman
*Assistant Examiner*—Dawayne A Pinkney
(74) *Attorney, Agent, or Firm*—Edwards Angell Palmer & Dodge LLP

(57) ABSTRACT

A fundus observation device is provided capable of capturing both images of the surface of the fundus oculi and tomographic images of the fundus oculi, and capable of preventing alignment indicators from being reflected in the image of the fundus oculi. Image forming part 220 operates to form surface images based on results of detecting the reflection light by the fundus oculi Ef of the illumination light obtained from a fundus camera unit 1A, and operates to form tomographic images based on results of detecting interference light LC by the OCT unit 150. The fundus camera unit comprises alignment optical systems 110A and 190A, which project an alignment indicator. Detection timing controlling part 210B controls a fundus camera unit 1A and makes it detect the illumination light substantially simultaneously with detection of the interference light. Before the interference light LC and illumination light are substantially simultaneously detected, the alignment controlling part 210 controls the alignment optical system 110A and 190A and terminates the projection of the alignment light indicator. Correction processing part 225 corrects the image position of tomographic images using the surface images obtained substantially simultaneously.

4 Claims, 17 Drawing Sheets

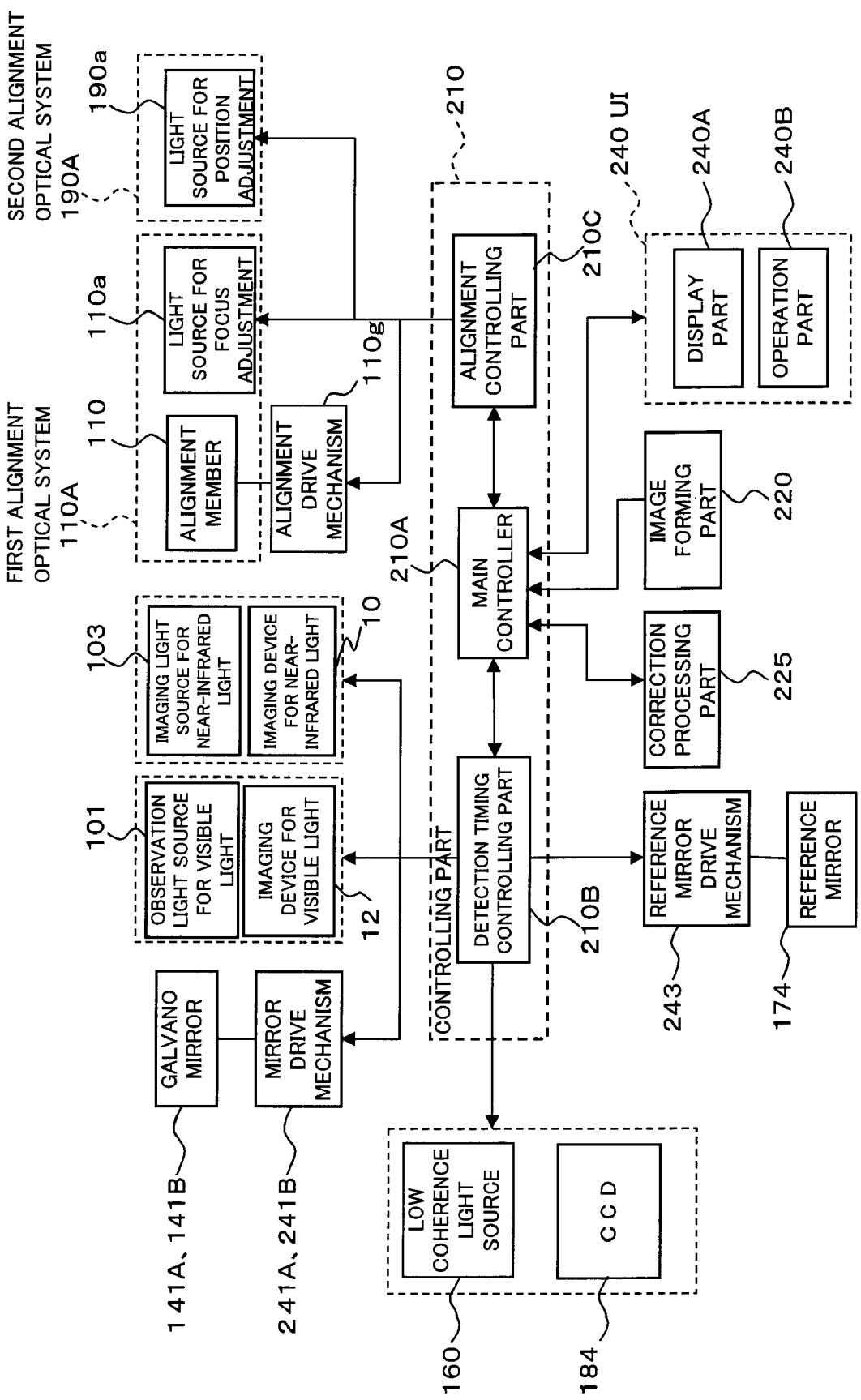

SURFACE IMAGE AND TOMOGRAPHIC IMAGE OF THE FUNDUS OCULI IN TIME t=t1

SURFACE IMAGE AND TOMOGRAPHIC IMAGE OF THE FUNDUS OCULI IN TIME t=t2

SURFACE IMAGE AND TOMOGRAPHIC IMAGE OF THE FUNDUS OCULI IN TIME t=t3

SURFACE IMAGE AND TOMOGRAPHIC IMAGE OF THE FUNDUS OCULI IN TIME t=t4

FUNDUS OBSERVATION DEVICE

BACKGROUND OF THE INVENTION

1. Field of the Invention

The present invention relates to a fundus observation device, for observing the state of the fundus oculi of an eye.

2. Description of the Related Art

As a fundus observation device, conventionally a fundus camera has been widely used. FIG. 13 shows one example of the appearance of a conventional fundus camera in general, and FIG. 14 shows one example of an optical system composition to be internally accommodated therein (e.g. JP Patent laid-open No. 2004-350849). Furthermore, "observation" is intended to include at least a case in which produced fundus images are observed (fundus observations with the naked eye may be included).

First, referring to FIG. 13, an explanation is made regarding the appearance of a conventional fundus camera 1000. This fundus camera 1000 is provided with a platform 3 mounted on a base 2 slidably in the front and rear, right and left (horizontal direction) directions. On this platform 3, an operation panel 3a and a control lever 4 are installed for an examiner to conduct various operations.

The examiner may place the platform 3 on the base 2 to be moved 3-dimensionally by operating the control lever 4. On the top of the control lever 4, an operation button 4a is installed to be pressed down to obtain fundus oculi images.

On the base 2, a post 5 is installed standing upwards. On the post 5, a jaw rest 6 where the jaw of a patient is to be rested and an external fixation lamp 7 as a light source for fixing an eye E are provided.

On the platform 3, a main body part 8 is installed to accommodate various optical systems or control systems of the fundus camera 1000. Furthermore, the control system may be installed inside the base 2 or the platform 3, etc., or in an external device such as a computer, etc. connected to the fundus camera 1000.

On the side of the eye E of the main body part 8 (the left side of the page in FIG. 13), an objective lens part 8a disposed opposite the eye E is installed. Also, on the examiner's side of the main body part 8 (the right side of the page in FIG. 13), an objective lens part 8b for observing the fundus oculi of the eye E with the naked is installed.

Furthermore, connected to the main body part 8 is a still camera 9 for producing a still image of a fundus oculi of the eye E and an imaging device 10 such as a TV camera, etc. for producing still images or moving images of a fundus oculi. The still camera 9 and the imaging device 10 are formed removably with respect to the main body part 8.

As a still camera 9, in accordance with various conditions such as the purpose of an examination or the saving method of produced images, etc., a digital camera equipped with imaging elements such as CCD (Charge Coupled Device) or CMOS (Complementary Metal Oxide Semiconductor), a film camera, and an instant camera, etc. may interchangeably be used when it is appropriate. The main body part 8 is equipped with a mounting part 8c for interchangeably mounting such a still camera 9.

If the still camera 9 or the imaging device 10 is for taking digital images, the image data of the produced fundus image may be sent to a device such as a computer, etc. connected to the fundus camera 1000 and be observed as a fundus image by being displayed on the display. Also, the image data can be sent to an image storing device connected to the fundus camera 1000 to compile a database and be used as electronic data for creating medical charts, etc.

Furthermore, on the examiner's side of the main body part 8, a touch panel monitor 11 is installed. On this touch panel monitor 11, fundus images of the eye E created based on the video signals output from the still camera 9 (a digital method thereof) or the imaging device 10 are displayed. Moreover, on the touch panel monitor 11, the xy coordinate system with the center of the screen as the origin is displayed overlapped with a fundus image. When the screen is touched by the examiner, the coordinate value corresponding to the touched position is displayed.

Next, referring to FIG. 14, a composition of an optical system of the fundus camera 1000 is described. The fundus camera 1000 is provided with an illuminating optical system 100 to light the fundus oculi Ef of an eye E, an imaging optical system 120 to guide the fundus reflection light of the illumination light to the eyepiece part 8b, a still camera 9, and an imaging device 10.

The illuminating optical system 100 comprises: an observation light source 101, a condenser lens 102, an imaging light source 103, a condenser lens 104, an exciter filter 105 and 106, a ring transparent plate 107, a mirror 108, a liquid crystal display (LCD) 109, an alignment member 110, a relay lens 111, an aperture mirror 112, and an objective lens 113.

The observation light source 101 consists of a halogen lamp, etc. and emits continuous light for observing the fundus. The condenser lens 102 is an optical element that converges the continuous light (observation illumination light) emitted by the observation light source 101 and substantially evenly irradiates the observation illumination light to the fundus oculi.

The imaging light source 103 consists of a xenon lamp, etc. to be flashed when producing fundus oculi Ef images. The condenser lens 104 is an optical element that converges the flash light (imaging illumination light) emitted by the imaging light source 103 and irradiates the fundus oculi Ef evenly with the imaging illumination light.

The exciter filters 105 and 106 are the filters to be used when fluorography of images of a fundus oculi Ef takes a place. The exciter filters 105 and 106 respectively can be inserted and retracted on the optical path by a drive mechanism such as a solenoid, etc. The exciter filter 105 is disposed on the optical path in the event of FAG (fluorescein angiography). Whereas, the exciter filter 106 is disposed on the optical path in the event of ICG (indocyanine green angiography). Furthermore, when color images are being obtained, both exciter filters 105 and 106 are retracted from the optical path.

The ring transparent plate 107 is disposed in a conjugating location with a pupil of the eye E, and is equipped with a ring transparent part 107a taking an optical axis of the illuminating optical system 100 as a center. The mirror 108 reflects the illumination light emitted by the observation light source 101 or by the imaging light source 103 in the direction of the optical axis of the imaging optical system 120. The LCD 109 displays a fixation target (not illustrated) for fixing the eye E.

An alignment member 110 is detachably built into the optical path of an illuminating optical system 100 manually. A first alignment optical system 110A having an optical path perpendicular to the optical path of the illuminating optical system 100 is built into the insert position of this alignment member 110. This first alignment optical system 110A is an optical system for projecting a split indicator used for the diopter scale (focus) adjustment for the fundus oculi Ef onto an eye (e.g., see JP Patent laid-open No. Hei 5-95906).

One example of the configuration of the first alignment optical system 110A is shown in FIG. 15. FIG. 15A is a side view of the first alignment optical system 110A, FIG. 15B is a side view of the alignment member 110, and FIG. 15C is a top view of the alignment member 110.

The alignment member 110 has an inclined surface 110s at the end on the side to be inserted into the optical path of the illuminating optical system 100 as shown in FIGS. 15B and C. This inclined surface 110s acts as a reflection mirror for reflecting light from the first alignment optical system 110A.

The first alignment optical system 110A comprises a light source 110a, a slit 110b, a collective lens 110c, a split prism 110d, a reflection mirror 110e, and a collective lens 110f as well as this alignment member 110 as shown in FIG. 15(A). The light source 110a may, for example, be a light-emitting diode (LED) for emitting light such as a near-infrared light (first alignment light). For example, a rectangle-shaped opening (slit) may be formed on the slit 110b.

The first alignment light emitted from the light source 110a passes through the opening of the slit 110b, is collected by the collective lens 110c, and is then injected into the split prism 110d. The split prism 110d splits this first alignment light into two light fluxes. The first alignment light having been split into two is respectively reflected by the reflection mirror 110c and focused on the inclined surface 110s of the alignment member 110 by the collective lens 110f. Then, the first alignment light is reflected by the inclined surface 110s, combined with the optical path of the illuminating optical system 100, and injected into the eye E via a relay lens 111, an aperture mirror 112, and an objective lens 113. These two first alignment lights are designed to coincide with each other on the focus surface.

The first alignment light injected into the eye E is reflected by the fundus oculi Ef, received at the image pick up element 10a via the imaging optical system 120, and then displayed on a touch panel monitor 11 (or an external display). The displaying feature of this first alignment light is shown in FIG. 17.

The symbol 110' in FIG. 17 indicates the shadow of an alignment member 110. In addition, the symbols L1 and L2 in FIG. 17 indicate bright lines which are based on the first alignment light reflected by the inclined surface 110s of the alignment member 110 (alignment bright lines). This pair of alignment bright lines L1 and L2 configures the split indicator described above.

When the fundus oculi Ef does not coincide with the focus surface, the alignment bright lines L1 and L2 are displayed with misaligned each other, i.e. they are misaligned laterally on the paper as shown in FIG. 17A. On the other hand, when the fundus oculi Ef coincides with the focus surface, the alignment bright lines L1 and L2 are displayed in the state in which the crosswise positions coincide with each other as shown in FIG. 17B. An examiner adjusts the focus such that the crosswise positions of the alignment bright lines L1 and L2 coincide with each other.

The aperture mirror 112 is an optical element to combine an optical axis of the illuminating optical system 100 and an optical axis of the imaging optical system 120. In the center region of the aperture mirror 112 an aperture part 112a is opened. The light axis of the illuminating optical system 100 and the light axis of the imaging optical system 120 arc to be crossed at a substantially central location of this aperture part 112a. The objective lens 113 is installed in the objective lens part 8a of the main body part 8.

The illuminating optical system 100 having such a composition illuminates a fundus oculi Ef in the following manner. First, the observation illumination light is emitted when the observation light source 101 is lit during fundus observation. This observation illumination light irradiates the ring transparent plate 107 through the condenser lenses 102 and 104. (The exciter filters 105 and 106 are retracted from the optical path.) The light passed through the ring transparent part 107a of the ring transparent plate 107 is reflected by the mirror 108 and is reflected along the optical axial direction of the imaging optical system 120 due to the aperture mirror 112 through the LCD 109 and the relay lens 111. The alignment member 110 has been manually retracted from the optical path in advance. The observing illumination light reflected by the aperture mirror 112 advances in the optical axial direction of the imaging optical system 120 and is converged by the objective lens 113, to be made incident onto the eye E, and illuminates the fundus oculi Ef.

Then, the ring transparent plate 107 is disposed in a conjugating location with the pupil of the eye E, and on the pupil a ring shaped image of the entering observation illumination light is formed. The fundus reflection light of the entered observation illumination light is to be emitted from the eye E through a central dark part of the ring image on the pupil. As described, it is to protect the effect of observing illumination light entering the eye E with respect to the fundus reflection light of the observing illumination light.

On the other hand, when imaging the fundus oculi Ef, flush light is emitted from the imaging light source 103 and the imaging illumination light is irradiated onto the fundus oculi Ef through the same path. In the event of photofluographing, either the exciter filter 105 or the exciter filter 106 is disposed selectively on the optical path depending on whether FAG imaging or ICG imaging is carried out. Furthermore, when imaging the fundus oculi Ef other than photofluography, or when observing the fundus oculi Ef, the exciter filter 105 and 106 are retracted from the optical path.

Whereas, imaging optical system 120 comprises: an objective lens 113, an aperture mirror 112 (an aperture part 112a thereof), an imaging diaphragm 121, a barrier filter 122 and 123, a focusing lens 124, half mirror 190, a relay lens 125, an imaging lens 126, a quick return mirror 127 and an imaging media 9a. Herein, the imaging media 9a is an arbitrary imaging media (image pick-up elements such as CCD, camera film, instant film, etc.) used for a still camera 9.

The fundus reflection light of the illumination light, emitted through the central dark part of the ring shaped image formed on the pupil from the eye E, enters the imaging diaphragm 121 through the aperture part 112a of the aperture mirror 112. The aperture mirror 112 reflects cornea reflection light of the illumination light and acts so as not to mix the cornea reflection light into the fundus reflection light made incident onto the imaging diaphragm 121. As a result, the generation of flare on the observation images and/or produced images is prevented.

The imaging diaphragm 121 is a plate shaped member at which plural circular light transparent parts of different sizes are formed. The plural light transparent parts constitute different diaphragms with different diaphragm values (F value), and are to be disposed alternatively on the optical path by a drive mechanism (not illustrated herein).

The barrier filters 122 and 123 can be inserted and retracted on the optical path by a drive mechanism such as a solenoid, etc. In the event of FAG imaging, the barrier filter 122 is disposed on the optical path while in the event of ICG imaging the barrier filter 123 is inserted onto the optical path. Furthermore, when imaging the fundus oculi Ef other than photofluography, or when observing the fundus oculi Ef, the barrier filters 122 and 123 are to be retracted from the optical path.

The focusing lens 124 is enabled to move in the light axial direction of the imaging optical system 120 by a drive mechanism (not illustrated herein). This movement of the focusing lens 124 allows to change the magnifying ratio in observation and the magnifying ratio in imaging, and to focus images of a fundus oculi (focus adjustment). The imaging lens 126 is a lens to focus the fundus reflection light from an eye E on the imaging media 9a.

The quick return mirror 127 is disposed rotatably around a rotary shaft 127a by a drive mechanism not illustrated herein. In the event of imaging a fundus oculi Ef with the still camera 9, the fundus reflection light is supposed to be guided to the imaging media 9a by springing up the quick return mirror 127 that is obliquely mounted on the optical path. Whereas, in the event of imaging a fundus oculi with an imaging device 10 or of observing the fundus oculi with the naked eye of the examiner, the quick return mirror 127 is to be obliquely mounted on the optical path to upwardly reflect the fundus reflection light.

The imaging optical system 120 is further provided, for guiding the fundus reflection light reflected by the quick return mirror 127, with a field lens 128, a switching mirror 129, an eyepiece 130, a relay lens 131, a reflection mirror 132, an imaging lens 133 and an image pick up element 10a. The image pick up element 10a is an image pick up element such as CCD, etc. installed internally in the imaging device 10. On the touch panel monitor 11 a fundus oculi image Ef' imaged by the image pick up element 10a is be displayed.

The switching mirror 129 is to be rotatable around the rotary shaft 129a as well as the quick return mirror 127. This switching mirror 129 is obliquely disposed on the optical path during observation with the naked eye and guides reflected light on the fundus oculi to the eyepiece 130.

Also, when a fundus image is formed by the imaging device 10, the switching mirror 129 is retracted from the optical path, and the fundus reflection light is guided toward an image pick-up element 10a. In this case, the fundus reflection light is directed toward a relay lens 131, is reflected by the mirror 132, and is focused on the image pick-up element 10a by the imaging lens 133.

A half mirror 190 is provided on the optical path between the focusing lens 124 and the relay lens 125 while the half mirror 190 is inclined. This half mirror 190 acts to combine the path of the second alignment optical system 190A shown in FIG. 16A with the path of the imaging optical system 120 (photographing optical path). This second alignment optical system 190A is an optical system for projecting a bright point (alignment bright point) used for the position adjustment (particularly adjustment of the working distance) of an optical system in relation to an eye E onto an eye E (e.g., see JP Patent laid-open No. Hei11-4808).

The second alignment optical system 190A comprises a light source 190a consisting of, for example, LED for emitting light such as a near-infrared light (second alignment light), a light guide 190b, a reflection mirror 190c, a two-hole aperture 190d, and a relay lens 190e as well as the half mirror 190.

The two-hole aperture 190d has two holes 190d1 and 190d2 as shown in FIG. 16B. The holes 190d1 and 190d2 are formed on, for example, the symmetric position for the center position 190d3 of the circular two-hole aperture 190d. The two-hole aperture 190d is arranged so that this center position 190d3 is located on the optical axis of the second alignment optical system 190A.

The second alignment light ejected from an ejection end 190β of the light guide 190b is reflected by the reflection mirror 190c and guided to the holes 190d1 and d2 of the two-hole aperture 190d respectively. The alignment lights that have passed the hole 190d1 and 190d2 are guided to the aperture mirror 112 by passing through the relay lens 190e and by being reflected by the half mirror 190. Then, the relay lens 190e focuses the image of the ejection end 190β of the light guide 190b on the center position of the hole 112a of the aperture mirror 112 (the position on the optical axis of the imaging optical system 120). The second alignment light that has passed through the hole 112a of the aperture mirror 112 is projected onto the cornea of the eye E via objective lens 113.

Herein, suppose that the positional relationship between the eye E and a fundus oculi camera 1000 (objective lens 113) is appropriate, i.e. that the distance from the eye E to the fundus oculi camera 1000 (working distance) is appropriate, and that the optical axis of the optical system of the fundus oculi camera 1000 and the eye axis of the eye E (top position of the cornea) are (almost) coincident with each other. In this case, two light fluxes (alignment light fluxes) formed by the two-hole aperture 190d are projected onto the eye E so as to be focused on the intermediate position between the top of the cornea and the center of corneal curvature. Meanwhile, when the working distance W from the eye E to the device main body is not appropriate, two alignment light fluxes will be separately projected onto the eye E, respectively.

The corneal reflection lights of the two alignment light fluxes (the second alignment light) are received by the image pick up element 10a via the imaging optical system 120. The photographed images by the image pick up element 10a are displayed on the touch panel monitor 11 (or an external display). The displaying feature of this second alignment light is shown in FIG. 17.

The symbol S in FIG. 17 indicates the scale having bracket shape, and symbols P1 and P2 indicate the light received image of two alignment light fluxes (alignment bright points). The scale S is displayed on the touch panel monitor 11 so that its center position coincides with the optical axis of the imaging optical system 120.

When the positional relationship between the eye E and the fundus oculi camera 1000 is not appropriate, the alignment bright points P1 and P2 are displayed in the state of being separated from each other as shown in FIG. 17A. Particularly, when the positions of the eye E and the fundus oculi camera 1000 are out of alignment together in the up-and-down direction or the right-and-left direction, the alignment bright points P1 and P2 are displayed at the position, in which they are out of alignment to the scale S in the up-and-down direction or the right-and-left direction.

On the other hand, when the positional relationship between the eye E and the fundus oculi camera 1000 is appropriate, the alignment bright points P1 and P2 are displayed in the scale S in the state of being overlapped with each other as shown in FIG. 17B. An examiner adjusts the positional relationship between the eye E and the fundus oculi camera 1000 such that the alignment bright points P1 and P2 overlap each other and are displayed on the scale S.

Such a fundus camera 1000 is a fundus observation device to be used for observing the state of the surface of a fundus oculi Ef, that is, the retina. In other words, a fundus camera 1000 is a fundus observation device to obtain a 2-dimensional fundus oculi image when it sees the fundus oculi Ef from the corneal direction onto the eye E. On the other hand, in the deep layer of retina tissues such as the choroidea or sclera exist, technology for observing these deep layer tissues has been desired, but, in recent years, devices for observing these deep layer tissues have been practically implemented (e.g. JP Patent laid-open No. 2003-000543, JP Patent laid-open No. 2005-241464).

The fundus observation device disclosed in JP Patent laid-open No. 2003-000543 and JP Patent laid-open No. 2005-241464 are devices to which so called OCT (Optical Coherence Tomography) technology is applied. With such fundus observation devices, low coherence light is split into two, one of which (signal light) is guided to a fundus oculi and the other one (reference light) is guided to a given reference object, and this is a device to form tomographic images of the surface and the deep layer tissue of a fundus oculi,and to form the 3-dimensional image from the tomographic images, by detecting and analyzing the interference light obtained by overlaying the signal light that has reached the fundus oculi and the reference light that has been reflected by the reference object. Such devices are in general called a Fourier domain OCT.

For such an optical image measuring device, the focus and position of the optical image measuring device in relation to the eye should be adjusted by using alignment indicators such as the same alignment bright line and alignment bright point as the fundus oculi camera 1000 described above.

In addition, the present inventors proposed a fundus observation device capable of capturing both images of the surface and tomographic images of the fundus oculi (e.g., see JP Patent Application No. 2006-003065 and JP Patent Application No. 2006-003878), but there was a disadvantage in that when an alignment indicator is projected onto the eye during capturing images of the surface of the fundus oculi, the image of the projected region cannot be observed. Particularly, as a configuration described in Patent Application No. 2006-003878, in the case of using an image of the surface of the fundus oculi to correct the position of a tomographic image, and when using an image of the surface of the fundus oculi into which an alignment indicator is reflected, correction may not be accomplished adequately.

The present invention is designed to solve such disadvantages and therefore is intended to provide a fundus observation device capable of capturing both images of the surface of the fundus oculi and tomographic images of the fundus oculi, and capable of preventing alignment indicators from being reflected in the image of the fundus oculi.

Particularly, the present invention is intended to provide technology that prevents alignment indicators from being reflected into the image of the surface of the fundus oculi, while the image is used for correcting the position of tomographic images of the fundus oculi.

SUMMARY OF THE INVENTION

The first aspect of the present embodiment is constructed as follows: a fundus observation device comprising: a first image forming part having an illuminating optical system configured to emit illumination light onto fundus oculi of an eye and an imaging optical system configured to detect the illumination light having reached said fundus oculi by the first detection part, wherein the first image forming part forms a 2-dimensional image of the surface of said fundus oculi based on the detection results by said first detection part; a second image forming part having a light source configured to emit low coherent light with a wavelength which is different from said illumination light; an interference optical generating part configured to split said emitted low coherent light into the signal light directed towards said fundus oculi and the reference light directed towards a reference object and to generate interference light by superposing the signal light having reached said fundus oculi and the reference light having reached said reference object; and a second detection part configured to detect said interference light generated, wherein said second image forming part forms tomographic images of said fundus oculi based on the detected results by said second detection part; an optical path combination and separation part configured to combine the photographing optical path formed by said imaging optical system and the optical path of a signal light directed toward said fundus oculi so as to illuminate said signal light onto said fundus oculi through said photographing optical path, and configured to separate said photographing optical path from the optical path of the signal light toward said fundus oculi so as to superpose said signal light on said reference light by said interference optical generating part; an alignment optical system configured to project an alignment indicator on said eye to preliminarily adjust a device for said eye; and a controlling part configured to control said alignment optical system to terminate projection of said alignment indicator on said eye before said illumination light is detected by said first detection part.

The first aspect of the present embodiment is constructed as follows: a first image forming part having an illuminating optical system configured to emit illumination light onto fundus oculi of an eye and a imaging optical system configured to detect the illumination light having reached said fundus oculi by the first detection part, wherein the first image forming part forms a 2-dimensional image of the surface of said fundus oculi based on the detection results by said first detection part; a second image forming part having a light source configured to emit light with a wavelength which is different from said illumination light; an interference optical generating part configured to split said light emitted from said light source into the signal light directed towards said fundus oculi and the reference light directed towards a reference object and to generate interference light by superposing the signal light having reached said fundus oculi and the reference light having reached said reference object; and a second detection part configured to detect said interference light generated, wherein said second image forming part forms tomographic images of said fundus oculi based on the detected results by said second detection part; an optical path combination and separation part configured to combine the photographing optical path formed by said imaging optical system and the optical path of a signal light directed toward said fundus oculi and so as to illuminate said signal light onto said fundus oculi through said photographing optical path, and configured to separate said photographing optical path from the optical path of the signal light having reached said fundus oculi so as to superpose said signal light on said reference light by said interference optical generating part; an alignment optical system configured to project an alignment indicator on said eye to preliminarily adjust a device for said eye; a detection timing controlling part configured to cause said first detection part to detect said illumination light substantially simultaneously with detection of said interference light by said second detection part; a controlling part configured to control said alignment optical system to terminate projection of said alignment indicator on said eye before said detection by said first detection part; and a correction part configured to correct the image position of the tomographic image of said fundus oculi according to a 2-dimensional image of the surface of said fundus oculi.

BRIEF DESCRIPTION OF THE DRAWINGS

FIG. 6 is a schematic block diagram representing one compositional example of a control system in an embodiment of the fundus observation device related to the present invention.

FIG. 7 is a schematic diagram representing one example of scanning features of signal light in an embodiment of the fundus observation device related to the present invention.

FIG. 15 is a schematic view of an example of the configuration of the alignment optical system of the conventional fundus observation device (fundus oculi camera).

FIG. 16 is a schematic view of an example of the configuration of the alignment optical system of a conventional fundus observation device (fundus oculi camera).

FIG. 17 is a schematic view of an example of the displaying feature of the alignment indicators according to the conventional fundus observation device (fundus oculi camera).

DETAILED DESCRIPTION OF THE REFERENCE EMBODIMENTS

Figure 13:
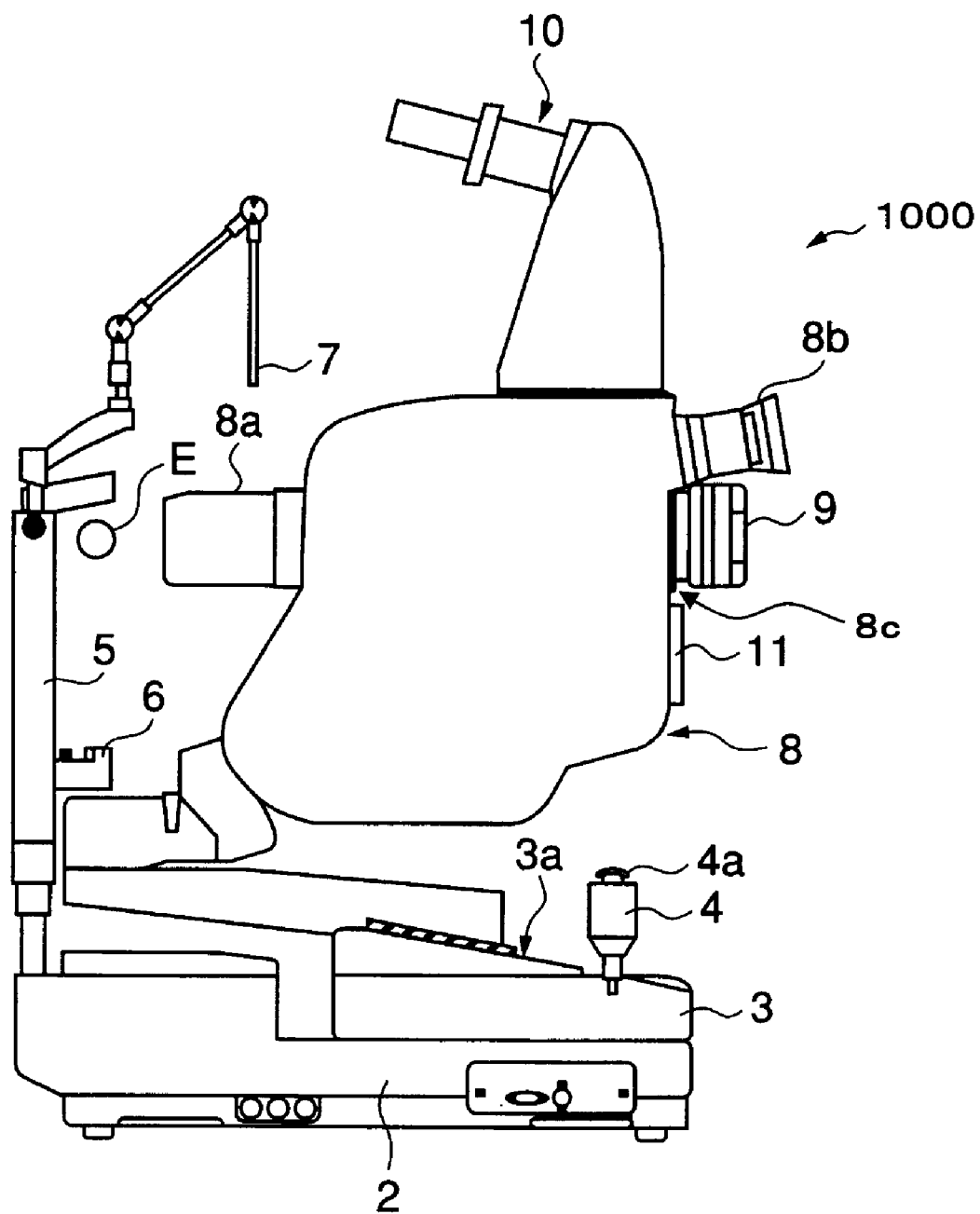
FIG. 13 is a schematic side view representing an appearance constitution of a conventional fundus observation device (fundus camera).
Figure 14:
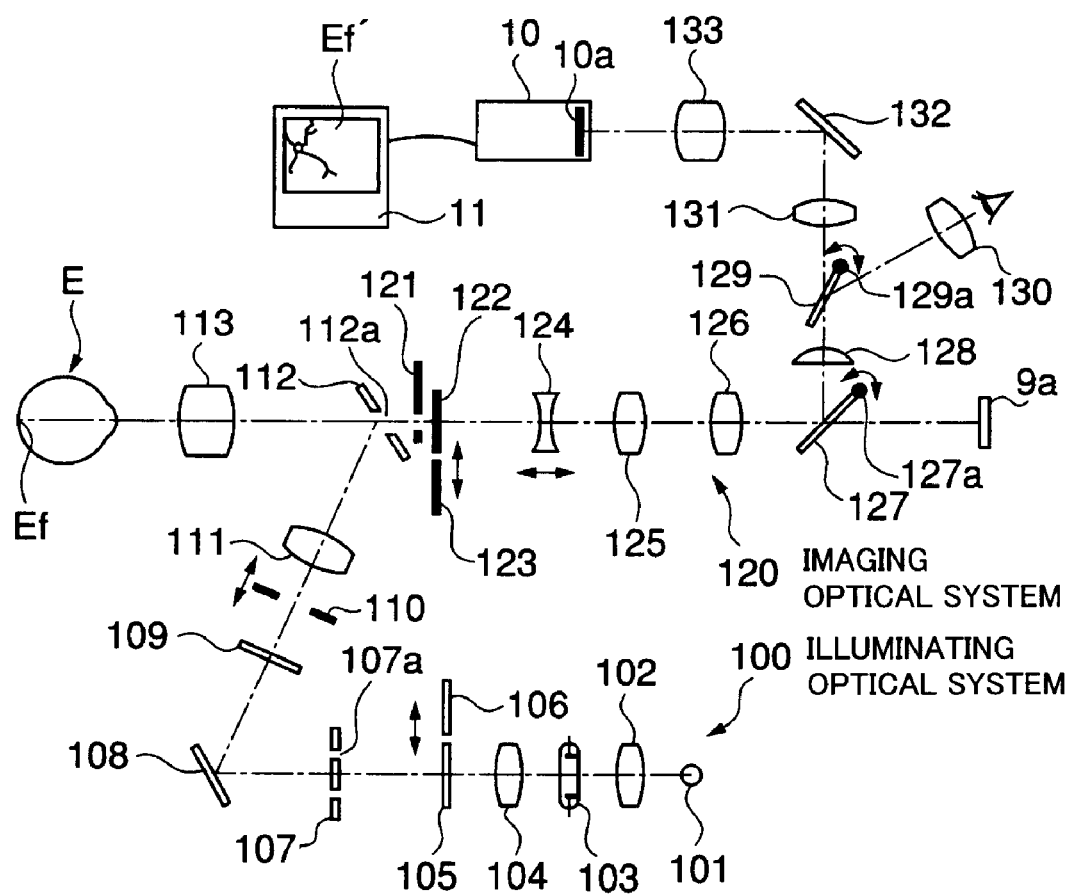
FIG. 14 is a schematic diagram representing one example of an internal constitution (an optical system constitution) of a conventional fundus observation device (fundus camera).

One example of favorable embodiments of a fundus observation device related to the present invention is described in detail referring to figures. Furthermore, for constitutional parts that are the same as conventional ones, the same symbols used in FIG. 13 and FIG. 14 are used.

In the present invention, "alignment indicator" shall refer to an indicator projected onto the eye for the task of the fundus observation device adjusting in relation to the eye prior to photographing a two-dimensional image of the surface of the fundus oculi or measuring a tomographic image. This alignment indicator has, for example, a split indicator used in the focus adjustment work to the eye (alignment bright line), an alignment bright point used in the adjustment work to the eye (work for matching the eye axis (top position of the cornea) of the eye and the optical axis of the optical system) and so on (described above).

Figure 1:
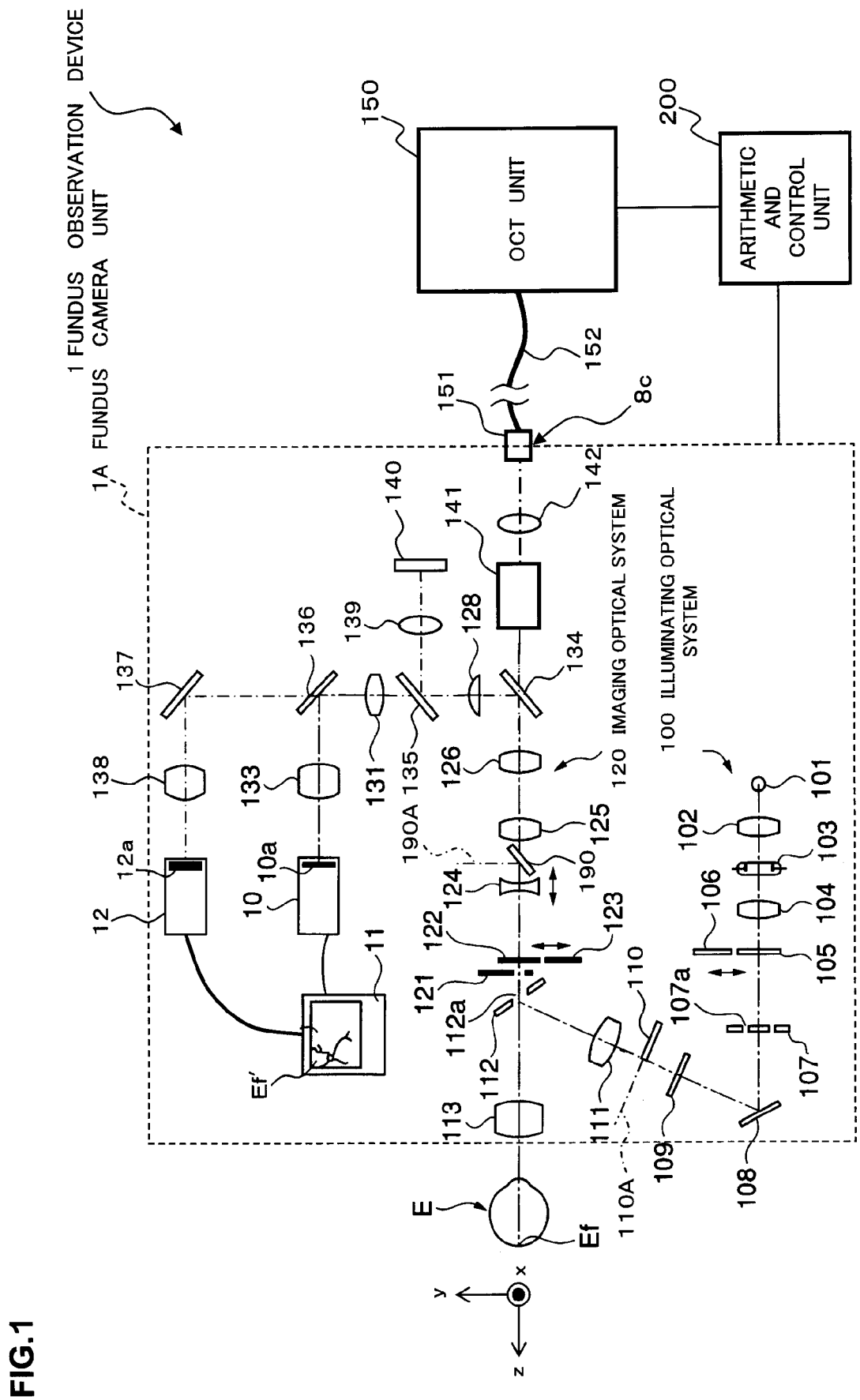
FIG. 1 is a schematic diagram representing one example of the entire constitution in an embodiment of the fundus observation device related to the present invention.
Figure 2:
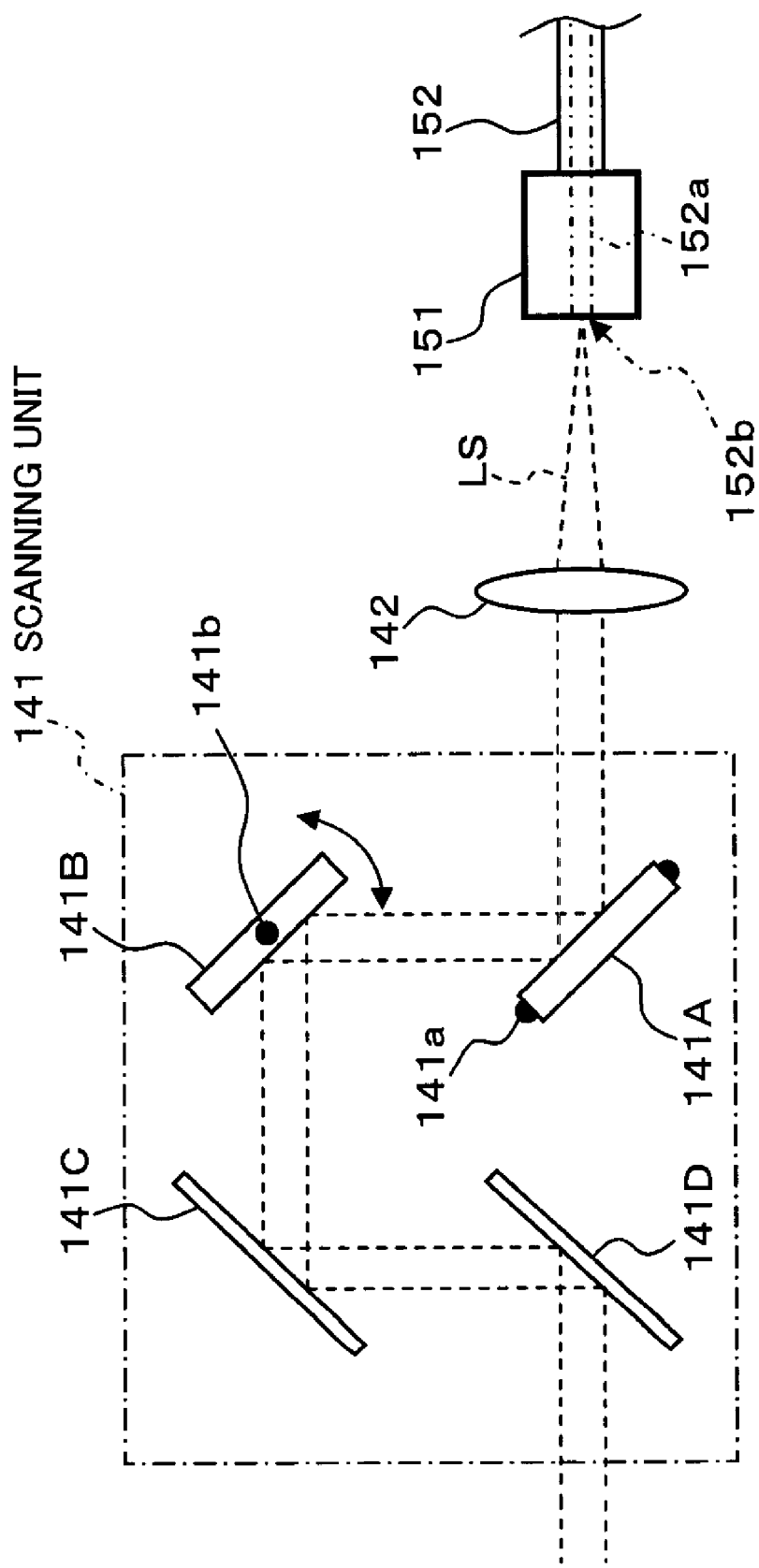
FIG. 2 is a schematic diagram representing one compositional example of a scanning unit installed in a fundus camera unit in an embodiment of the fundus observation device related to the present invention.
Figure 3:
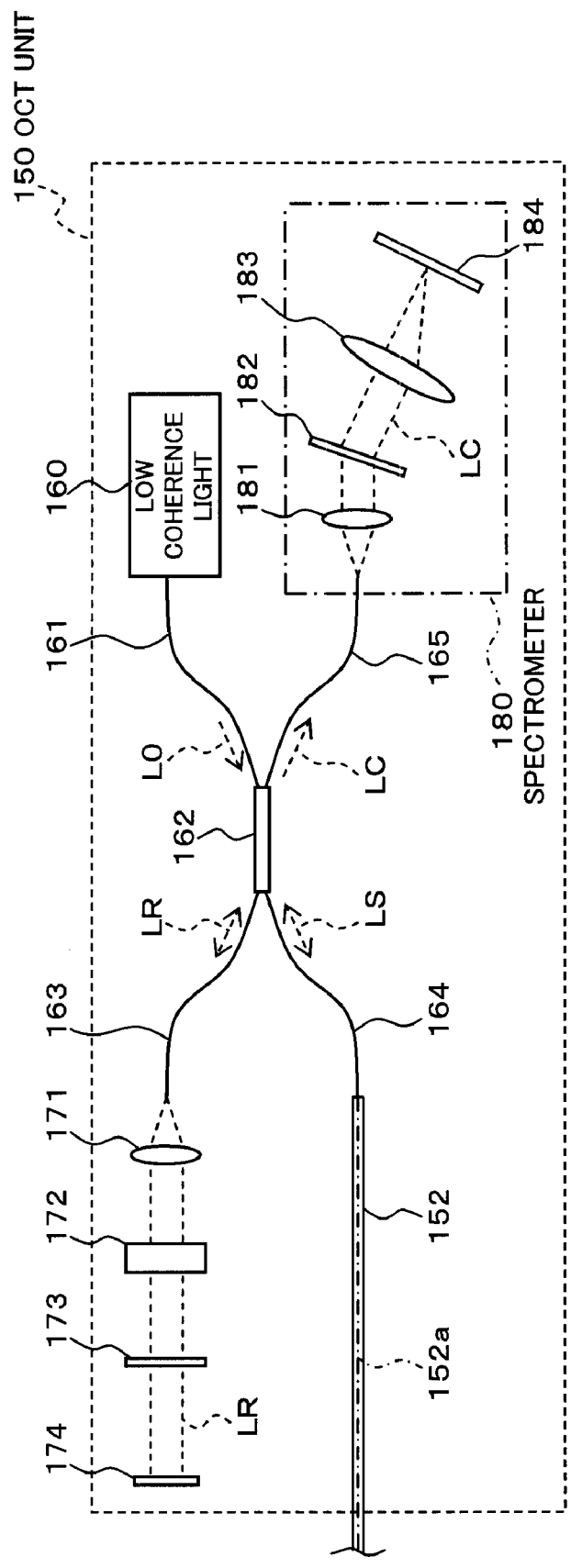
FIG. 3 is a schematic diagram representing one compositional example of an OCT unit in an embodiment of the fundus observation device related to the present invention.
Figure 4:
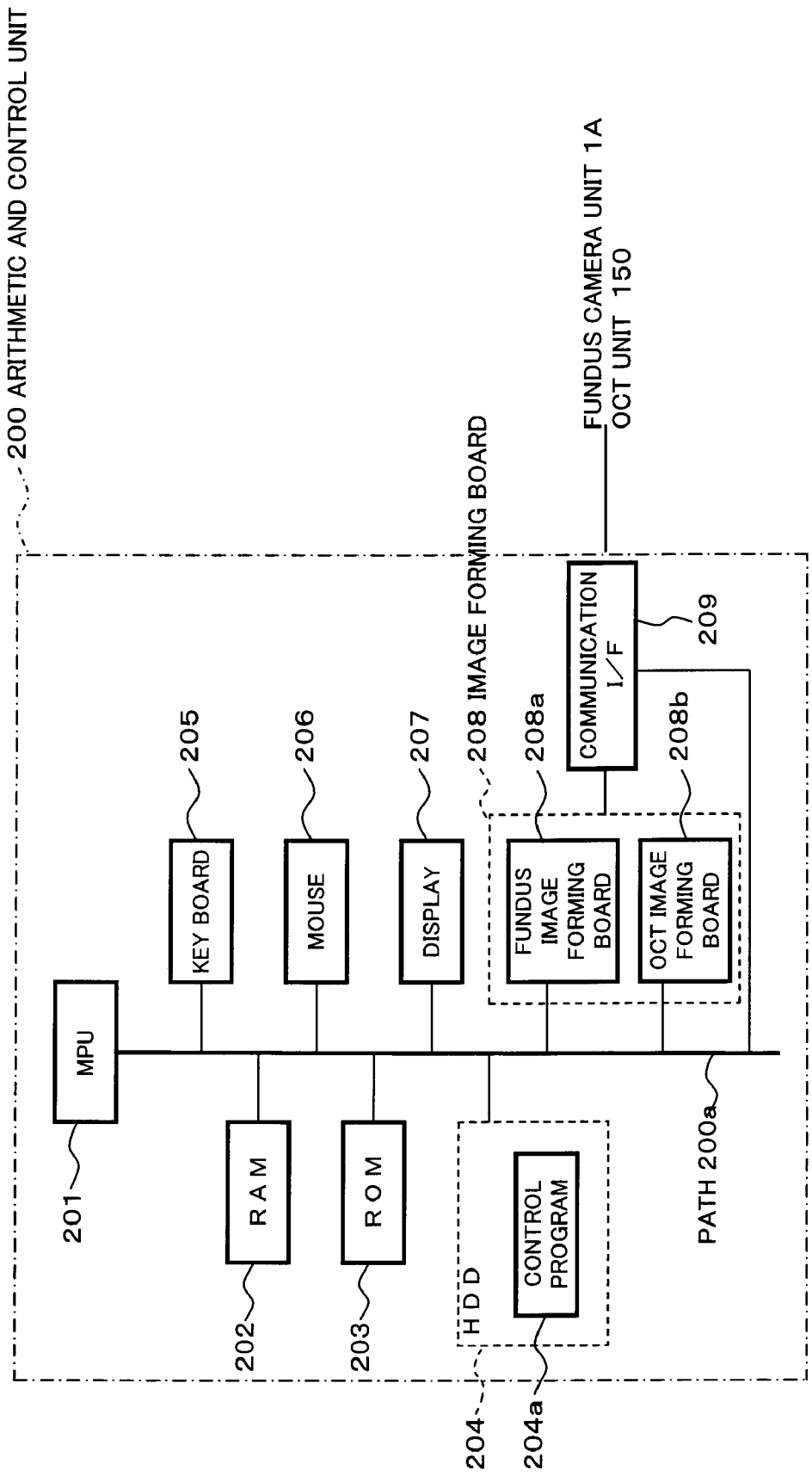
FIG. 4 is a schematic block diagram representing one example of hardware configurations of an arithmetic and control unit in an embodiment of the fundus observation device related to the present invention.
Figure 5:
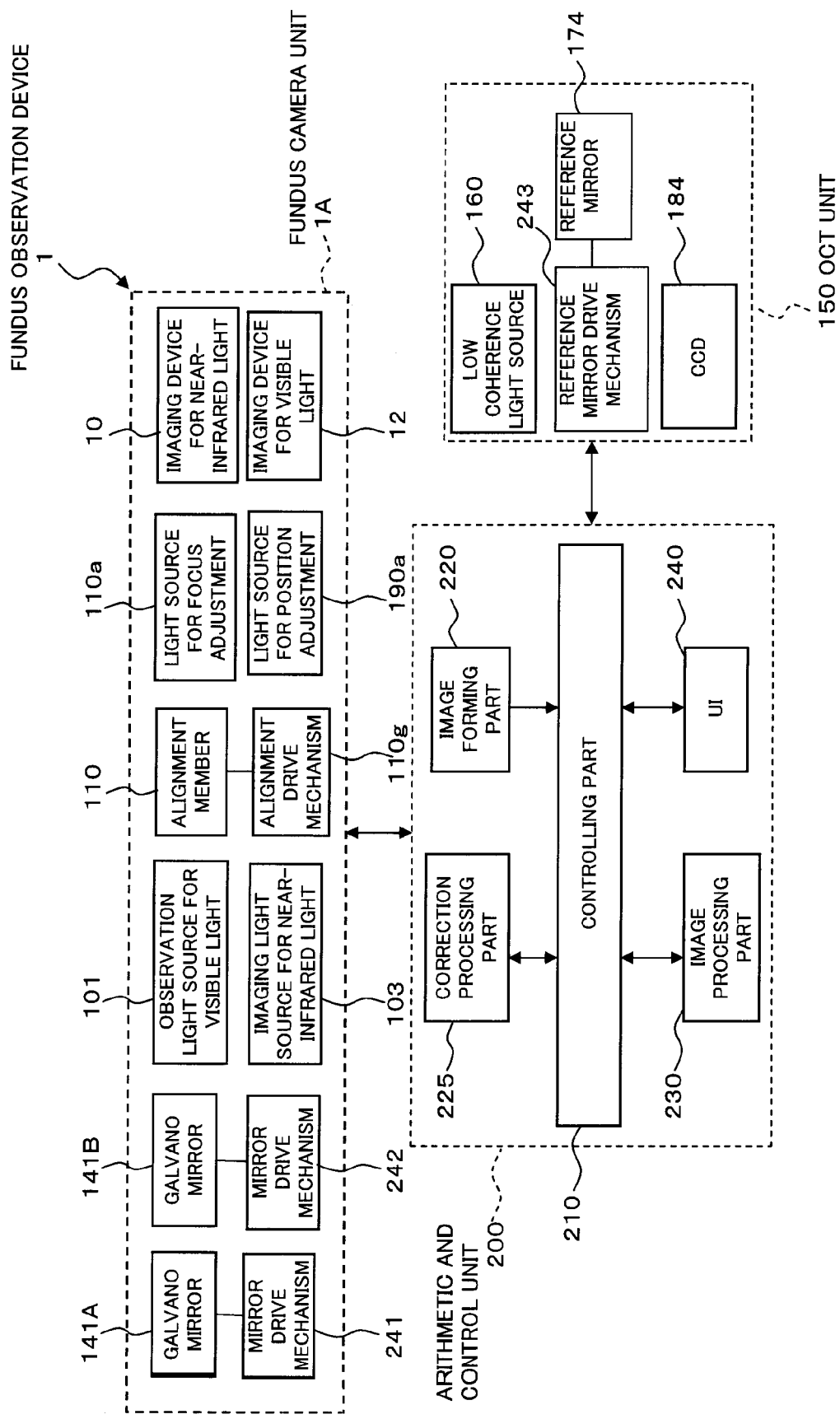
FIG. 5 is a schematic block diagram representing one compositional example of a control system in an embodiment of the fundus observation device related to the present invention.

First, by referring to FIG. 1 through FIG. 6, the constitution of the fundus observation device related to the present invention is described. FIG. 1 shows the entire constitution of the fundus observation device I related to the present invention. FIG. 2 shows a constitution of a scanning unit 141 in a fundus camera unit IA. FIG. 3 shows a constitution of an OCT unit 150. FIG. 4 shows a hardware configuration of an arithmetic and control unit 200. FIG. 5 and FIG. 6 show a configuration of a control system of the fundus observation device 1.

The Entire Constitution

As shown in FIG. 1, the fundus observation device 1 is comprised of a fundus camera unit 1A that functions as a fundus camera, an OCT unit 150 accommodating the optical system of an optical image measuring device (OCT device), and an arithmetic and control unit 200 that executes various arithmetic processes and control processes, etc.

The fundus observation device 1 is a component of one example of the "the first image forming part" with the arithmetic and control unit 200. The OCT unit 150 is a component of one example of the "the second image forming part" with the arithmetic and control unit 200. Further, this "the second image forming part" also includes each optical element through the signal light such as a scanning unit 141 provided in the fundus camera unit 1A, etc.

To the OCT unit 150, one end of a connection line 152 is attached. To the other end of this connection line 152, a connector part 151 is attached. This connector part 151 is attached to a mounting part 8c shown in FIG. 13. Furthermore, a conductive optical fiber runs through the inside of the connection line 152. The OCT unit 150 and the fundus camera unit 1A are optically connected through the connection line 152. The constitution details of the OCT unit 150 are to be described later referring to FIG. 3.

Constitution of Fundus Camera Unit

The fundus camera unit 1A has substantially the same appearance as the conventional fundus camera 1000 shown in FIG. 13. Furthermore, as in the conventional optical system shown in FIG. 14, the fundus camera unit 1A is provided with an illuminating optical system 100 to light a fundus oculi Ef of an eye E, and an imaging optical system 120 for guiding the fundus reflection light of the illumination light to an imaging device 10.

In addition, although the details are to be described later, an imaging device 10 in an imaging optical system 120 of the present embodiment is used for detecting the illumination light with a wavelength in the near-infrared region. Furthermore, in this imaging optical system 120, an imaging device 12 for detecting the illumination light with a wavelength in the visible region is provided separately. In addition, in this imaging optical system 120, it can guide the signal light from the OCT unit 150 to the fundus oculi Ef and the signal light through the fundus oculi Ef to the OCT unit 150.

Also, the illuminating optical system 100 is comprised as in conventional ones including: an observation light source 101, a condenser lens 102, an imaging light source 103, a condenser lens 104, an exciter filter 105 and 106, a ring transparent plate 107, a mirror 108, an LCD 109, an alignment member 110, a relay lens 111, an aperture mirror 112, and an objective lens 113.

The observation light source 101, for example, emits the illumination light of a wavelength in the visible region included within about 400 nm to 700 nm. Furthermore, the imaging light source 103, for example, emits the illumination light of a wavelength in the near-infrared region included within about 700 nm to 800 nm. The near-infrared light emitted from this imaging light source 103 is provided shorter than the wavelength of the light used by the OCT unit 150 (to be described later).

Figure 15A:
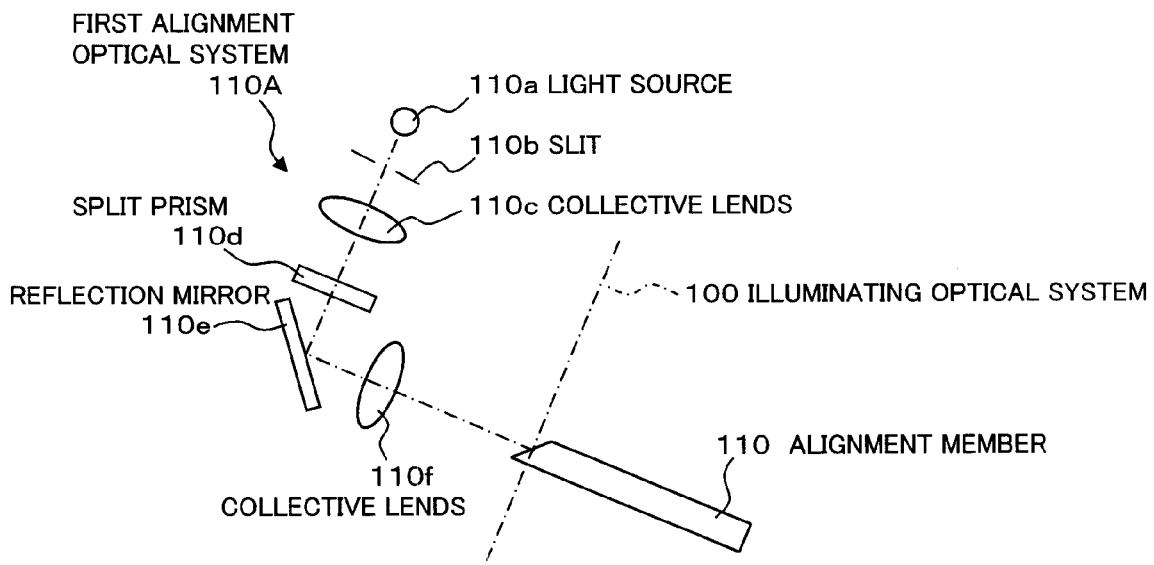
FIG. 15A is a side view of an example of the configuration of the optical system for projecting split indicators used for the focus adjustment onto an eye.
Figure 15B:
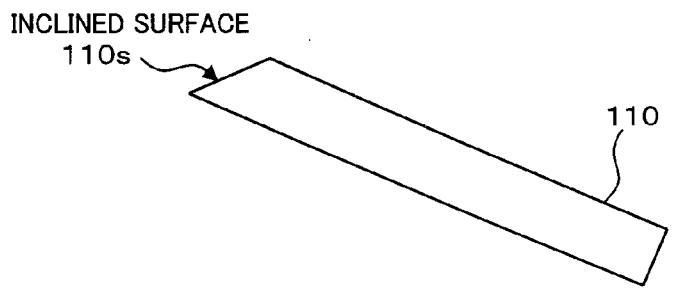
FIG. 15B is a side view of an example of the configuration of an alignment member.
Figure 15C:
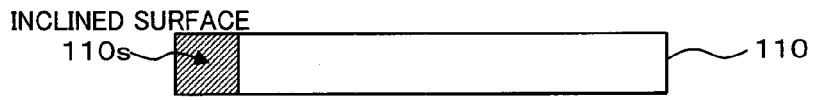
FIG. 15C is a top view of an example of the configuration of an alignment member.

The alignment member 110 has an inclined surface 110s at the end which is on the side to be inserted to the optical path of the illuminating optical system 100 as shown in FIG. 15B and FIG. 15C. This inclined surface 110s acts as a reflection mirror for reflecting light from the first alignment optical system 110A shown in FIG. 15A (first alignment light). Incidentally, the inclined surface 110s has an area sufficiently small compared to the cross-section area of the illuminating light at its insert position. In addition, the alignment member 110 inserted onto the optical path is positioned such that the center position of the inclined surface 110s is on the optical axis of the illuminating optical system 100.

Figure 17A:
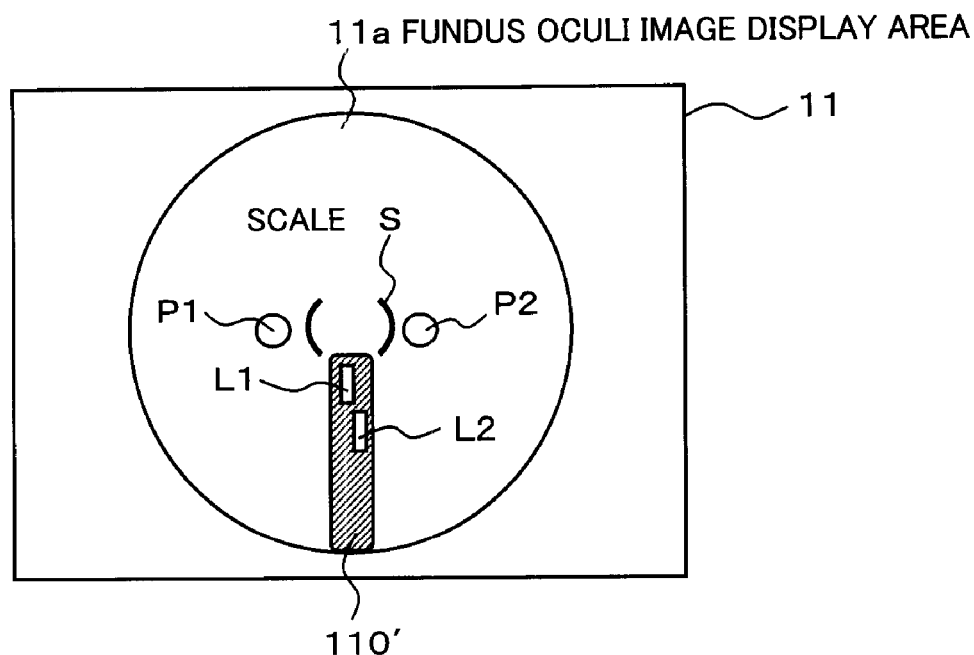
FIG. 17A shows the displaying feature of split indicators in an unfocused state and the displaying feature of alignment bright points and scales in the state in which the position of the device does not coincide with an eye.
Figure 17B:
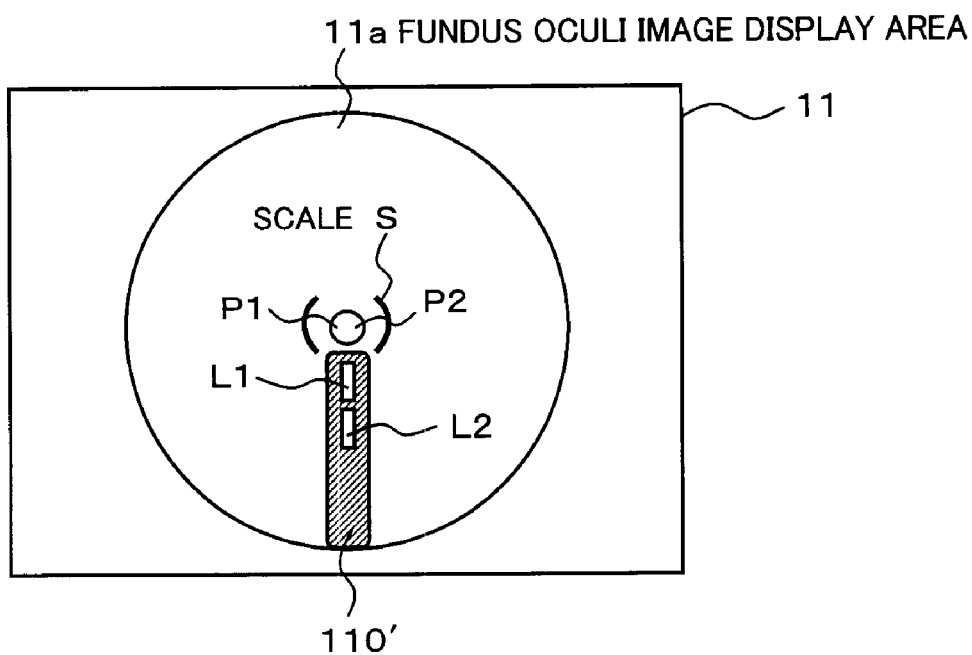
FIG. 17B shows the displaying feature of split indicators in the focused state and the displaying feature of alignment bright points and scales in the state in which the position of the device coincides with an eye.

This first alignment optical system 110A is an optical system for projecting split indicators used for the focus adjustment to the fundus oculi Ef (alignment bright lines L1 and L2; see FIG. 17) onto an eye E.

The first alignment optical system 110A comprises an alignment member 110, a light source 110a for emitting the first alignment light (e.g., near-infrared light with the wavelength of approximately 700 nm to 800 nm), a slit 110b, a collective lens 110c, a split prism 110d, a reflection mirror 110e, and a collective lens 110f, as shown in FIG. 15A.

The split indicators (referred to as "L1" and "L2") are indicators equivalent to one example of the "first alignment indicator" relating to the present invention. In addition, the light source 110a is equivalent to one example of the "first alignment light source" relating to the present invention, and (the inclined surface 110s of) the alignment member 110 is equivalent to one example of the "first optical path combination part" relating to the present invention.

The alignment member 110 is inserted in and/or detached from the optical path by being moved using the following alignment drive mechanism 110g to be described. As a moving feature of the alignment member 110, the alignment member 110 may, for example, be moved in parallel in the direction perpendicular to the optical path, or be moved rotationally centering around the end on the side opposite to the inclined surface 110s. Incidentally, it is also possible to configure the alignment member 110 to be inserted in and/or detached from the optical path by configuring the alignment optical system 110A in an integrated fashion as a unit and by moving this unit.

At the same time, the imaging optical system 120 comprises: an objective lens 113, an aperture mirror 112 (aperture part 112a thereof), an imaging diaphragm 121, a barrier filter 122 and 123, a focusing lens 124, a half mirror 190, a relay lens 125, an imaging lens 126, a dichroic mirror 134, a field lens 128, a half mirror 135, a relay lens 131, a dichroic mirror 136, an imaging lens 133, an imaging device 10 (an image pick-up element 10a), a reflection mirror 137, an imaging lens 138, an imaging device 12 (an image pick-up element 12a), and a lens 139 and LCD (Liquid crystal Display) 140.

Focusing lens 124 is designed to move in the direction of the optical axis of the imaging optical system 120 in response to, for example, operations for a focusing operating part such as a knob (focusing knob) or the like provided on the package of the fundus camera unit 1A. Incidentally, a mechanism for moving the focusing lens 124 may consist of only a mechanical mechanism such as a gear, or may be a configuration to which an electrical member such as a motor would be added.

Figure 16A:
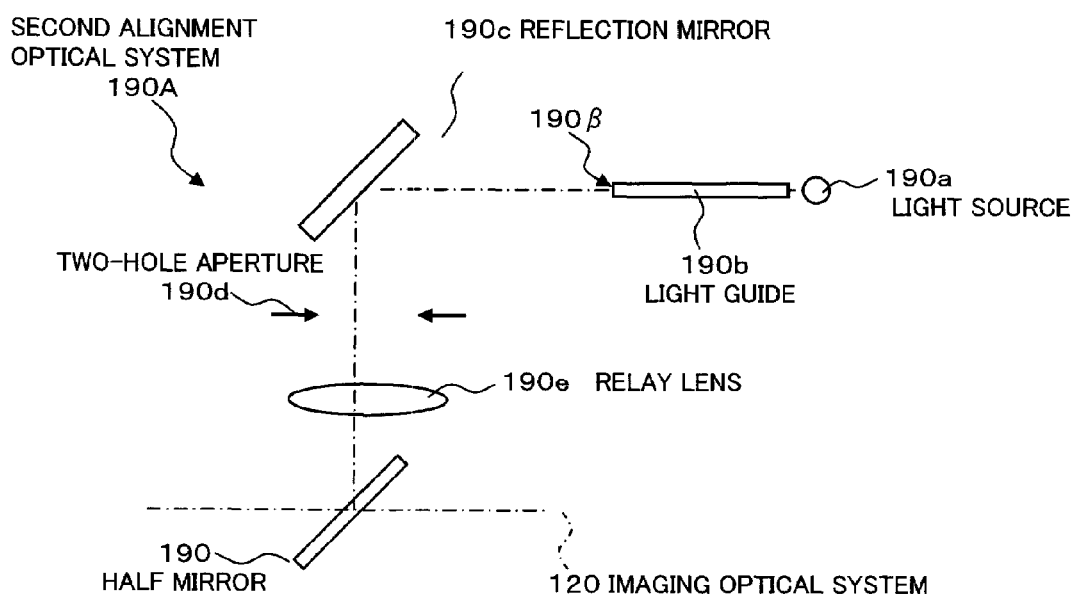
FIG. 16A is a side view of an example of the configuration of the optical system for projecting a pair of alignment bright points used for the position adjustment of the device in relation to an eye onto the eye.
Figure 16B:
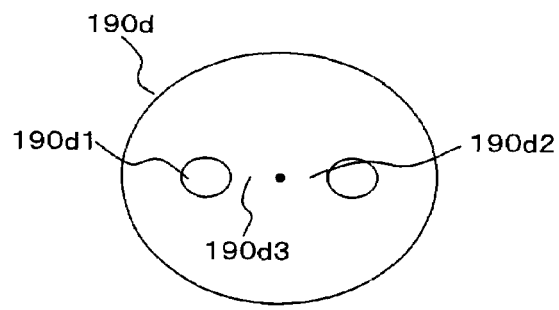
FIG. 16B is a top view of an example of the configuration of a two-hole aperture.

The half mirror 190 acts to combine the optical path of the second alignment optical system 190A shown in FIG. 16A with the optical path of the imaging optical system 120 (photographing optical path). This second alignment optical system 190A comprises a half mirror 190, a light source 190a for emitting a second alignment light (e.g., near-infrared light with the wavelength of approximately 700 nm to 800 nm), a light guide 190b, a reflection mirror 190c, a two-hole aperture 190d, and a relay lens 190e. The two-hole aperture 190d has two holes 190d1 and 190d2 as shown in FIG. 16B.

This second alignment optical system 190A is an optical system for projecting a pair of alignment bright points P1 and P2 (see FIG. 17) onto an eye E, the pair being used in the adjustment work of the position of the device to the eye, that is, in the work for matching the optical axes of the illuminating optical system 100 and the imaging optical system 120 to the eye axis (top position of the cornea) of the eye E.

The alignment bright points P1 and P2 are the indicators equivalent to one example of the "second alignment indicators" relating to the present invention. In addition, the light source 190a is equivalent to one example of the "second alignment light source" relating to the present invention, and the half mirror 190 is equivalent to one example of the "second optical path combination part" relating to the present invention.

The imaging optical system 120 related to the present embodiment is different from the conventional imaging optical system 120 shown in FIG. 14 in that the dichroic mirror 134, the half mirror 135, a dichroic mirror 136, the reflection mirror 137, the imaging lens 138, and the lens 139 and LCD 140 are provided.

The dichroic mirror 134 reflects the fundus reflection light of the illumination light (with a wavelength included within about 400 nm to 800 nm) from the illuminating optical system 100, and transmits the signal light LS (with a wavelength included within about 800 nm to 900 nm; to be described later) from the OCT unit 150. This dichroic mirror 134 is the equivalent of one example of the "optical combination and separation part" relating to the present invention.

Furthermore, the dichroic mirror 136 transmits the illumination light with a wavelength in the visible region from the illuminating optical system 100 (the visible light of a wavelength within about 400 nm to 700 nm for emitting from the observation light source 101), and reflects the illumination light with a wavelength in the near-infrared region (the near-infrared light of a wavelength within about 700 nm to 800 nm for emitting from the imaging light source 103). Therefore, illumination light with the wavelength in the visible region will be guided to the imaging device 12 and illumination light with the wavelength in the near-infrared region will be guided to the imaging device 10.

Incidentally, the first and second alignment lights passing through the eye E will be reflected by a dichroic mirror 134 and a dichroic mirror 136 so as to be guided to the imaging device 10.

The LCD 140 shows an internal fixation target, etc. The light from this LCD 140 is reflected by the half mirror 135 after being converged by the lens 139, and reflects the dichroic mirror 136 through the field lens 128. Further, it enters the eye E passing through the imaging lens 126, the relay lens 125, the half mirror 190, the focusing lens 124, the aperture mirror 112 (aperture part 112a thereof), the objective lens 113, etc. As a result, an internal fixation target, etc. is displayed in a fundus oculi Ef of an eye E.

The image pick up element 10a is the image pick up element of CCD and CMOS, etc. installed internally in an imaging device 10 such as a TV camera, and is particularly used for detecting light of a wavelength in the near-infrared region (that is, the imaging device 10 is the infrared TV camera for detecting near-infrared light). The imaging device 10 outputs the image signal as a result of detecting near-infrared light. A touch panel monitor 11 displays a 2-dimensional image (fundus image Ef') of the surface of the fundus oculi Ef based on this image signal. Also, this image signal is sent to the arithmetic and control unit 200, and the fundus oculi image is displayed on the display (to be described later). Furthermore, when the fundus oculi are being imaged by this imaging device 10, the illumination light emitted from the imaging light source 103 of the illuminating optical system 100, having a wavelength in the near-infrared region, is used. This (image pick up element 10a of) imaging device 10 is equivalent to one example of "the first detection part" relating to the present invention.

Also, the image pick up element 12a is the image pick up element of CCD and CMOS, etc. installed internally in an imaging device 12 such as a TV camera, and is particularly used for detecting light of a wavelength in the visible region (that is, the imaging device 12 is the TV camera for detecting visible light). The imaging device 12 outputs the image signal as a result of detecting visible light. A touch panel monitor 11 displays a 2-dimensional image (fundus image Ef') of the surface of the fundus oculi Ef based on this image signal. Also, this image signal is sent to the arithmetic and control unit 200, and the fundus oculi image is displayed on the display (to be described later). Furthermore, when the fundus oculi are being imaged by this imaging device 12, the illumination light emitted from the observation light source 101 of the illuminating optical system 100, having a wavelength in the near-infrared region, is used. This (image pick up element 12a of) imaging device 12 is equivalent to one example of "the first detection part" relating to the present invention when the light having a wavelength in the near-infrared region is used as the first and second alignment light.

Furthermore, the imaging optical system 120 of the present embodiment is provided with a scanning unit 141 and a lens 142. The scanning unit 141 is equipped with a constitution to scan the light output (signal light LS; to be described later) from the OCT unit 150 on a fundus oculi Ef.

The lens 142 incidents the signal light LS from the OCT unit 150 in the form of parallel light flux onto the scanning unit 141. Furthermore, the lens 142 acts so as to converge the fundus reflection light of the signal light LS that has reached through the scanning unit 141.

In FIG. 2, one example of a concrete constitution of the scanning unit 141 is shown. The scanning unit 141 is comprised including Galvano mirrors 141A, 141B, and reflection mirrors 141C, 141D.

The Galvano mirrors 141A and 141B are to be rotatable centering around rotary shafts 141a and 141b respectively. The rotary shaft 141a and 141b are arranged perpendicular to each other. In FIG. 2, the rotary shaft 141a of the Galvano mirror 141A is arranged parallel to the paper face, while the rotary shaft 141b of the Galvano mirror 141B is arranged perpendicular to the paper face. That is, the Galvano mirror 141B is to be rotatable in the directions indicated by an arrow pointing in both directions in FIG. 2, while the Galvano mirror 141A is to be rotatable in the directions perpendicular to the arrow pointing in both directions. As a result, this pair of Galvano mirrors 141A and 141B act so that the reflecting direction of the signal light LS changes to a direction perpendicular to each other. Furthermore, the rotary movement of the Galvano mirror 141A and 141B respectively is driven by a drive mechanism (see FIG. 5) to be described later.

The signal light LS reflected by the Galvano mirrors 141A and 141B is to be reflected by reflection mirrors 141C and 141D, and is to advance in the same direction as having entered into the Galvano mirror 141A As described previously, a conductive optical fiber 152a runs inside the connection line 152, and the end face 152b of the optical fiber 152a is arranged opposing the lens 142. The signal light LS emitted from this end face 152b advances while gradually expanding its beam diameter toward the lens 142 until being converged to a parallel light flux by this lens 142. On the contrary, the fundus reflection light of the signal light LS is converged toward the end face 152b by this lens 142.

Constitution of OCT Unit

Next, referring to FIG. 3, the constitution of an OCT unit 150 is described. The OCT unit 150 shown in FIG. 3 has substantially the same optical system as a conventional optical image measuring device, and is equipped with an interferometer that splits the light emitted from a light source into reference light and signal light, and generates interference light by the reference light that has passed through a reference object and the signal light that has passed through an object to be measured (fundus oculi Ef).

A low coherence light source 160 is composed of a broad band light source such as super luminescent diode (SLD) or a light emitting diode (LED), etc that emits low coherence light L0. This low coherence light L0, for instance, has a wave length in the near-infrared region and is supposed to be light having a time wise coherence length of approximately several tens of micro-meters. The low coherence light L0 emitted from the low coherence light source 160 has a longer wavelength than the illumination light (wavelength: about 400 nm to 800 nm) of the fundus camera unit 1A, for example, a wavelength included within about 800 nm to 900 nm. This low coherence light source 160 corresponds to an example of the "light source" relating to the present invention.

The low coherence light L0 emitted from the low coherence light source 160 is guided to an optical coupler 162 through an optical fiber 161 composed of, e.g. a single mode fiber, or PM (Polarization maintaining) fiber, and then split into reference light LR and signal light LS.

Furthermore, the optical coupler 162 has both actions, i.e. splitting lights (as a splitter), and superposing lights (as a coupler); however, herein conventionally referred to as an "optical coupler".

The reference light LR generated by the optical coupler 162 is guided by an optical fiber 163 consisting of such as a single mode fiber, and emitted from the end face of the fiber. The emitted reference light LR is reflected by a reference mirror 174 (reference object) through a glass block 172 and a density filter 173 after having been converged into a parallel light flux by a collimator lens 171.

The reference light LR reflected by the reference mirror 174 is converged to the end face of the optical fiber 163 by the collimator lens 171 again through the density filter 173 and the glass block 172. The converged reference light LR is guided to the optical coupler 162 through the optical fiber 163.

Furthermore, the glass block 172 and the density filter 173 act as a delaying device for matching the optical path length (optical distance) between the reference light LR and the signal light LS, and as a device for matching the dispersion characteristics of reference light LR and the signal light LS.

Furthermore, the reference mirror 174 is provided to be movable in the propagating direction of the reference light LR. As a result, it ensures the light path length of the reference light LR according to the axial length, etc. of an eye E. Moreover, the reference mirror 174 is operated to move by a drive mechanism including a motor, etc.

Whereas, the signal light LS generated by the optical coupler 162 is guided to the end part of the connection line 152 by an optical fiber 164 consisting of such as a single mode fiber. A conductive optical fiber 152a runs inside the connection line 152. Herein, the optical fiber 164 and the optical fiber 152a may be composed of a single optical fiber, or may be jointly formed by connecting each end. In either case, it is sufficient as long as the optical fiber 164 and 152a are composed so as to be capable of transferring the signal light LS between the fundus camera unit 1A and the OCT unit 150.

The signal light LS is guided within the connection line 152 to the fundus camera unit 1A. Then, the signal light LS enters into the eye E through the lens 142, the scanning unit 141, the dichroic mirror 134 the imaging lens 126, the relay lens 125, the half mirror 190, the focusing lens 124, the imaging diaphragm 121, the aperture part 112a of an aperture mirror 112, and the objective lens 113 (then, the barrier filter 122 and 123 are retracted from the optical path respectively).

The signal light LS that has entered into the eye E forms an image on a fundus oculi (retina) Ef and is then reflected. Then, the signal light LS is not only reflected on the surface of the fundus oculi Ef, but is also scattered at the refractive index boundary reaching the deep area of the fundus oculi Ef. As a result, the signal light LS reached the fundus Ef becomes a light containing the information reflecting the surface state of the fundus oculi Ef and the information reflecting the scattered state in the rear at the refractive index boundary of the deep area tissue. The light is simply referred as "fundus reflection light of the signal light LS.

The fundus reflection light of the signal light LS advances reversely on the above path and converges at the end face 152b of the optical fiber 152a, then enters into the OCT unit 150 through this optical fiber 152a, and returns to the optical coupler 162 through the optical fiber 164. The optical coupler 162 overlays this signal light LS on the reference light LR reflected at the reference mirror 174 to generate interference light LC. The generated interference light LC is guided into a spectrometer 180 through an optical fiber 165 consisting of such as a single mode fiber.

Herein, the "interference light generation part" in the present invention is comprised of an interferometer including at least an optical coupler 162, an optical fiber 163 and 164, and a reference mirror 174. Furthermore, although a Michelson type interferometer has been adopted in the present embodiment, for instance, a Mach Zender type, etc. or any optional type of interferometer may be adopted appropriately.

The spectrometer 180 is comprised of a collimator lens 181, a diffraction grating 182, an image forming lens 183, and a CCD (Charge Coupled Device) 184. The diffraction grating 182 in the present embodiment is a transmission type diffraction grating; however, needless to say, a reflection type diffraction grating may also be used. Furthermore, in place of CCD 184, it is also possible to adopt other photo-detecting elements such as CMOS etc. This type of photo-detecting element that detects the interference light LC is equivalent to the one example of the "second detecting part" relating to the present invention.

The interference light LC entered the spectrometer 180 is to be resolved into spectra by the diffraction grating 182 after having been converged into a parallel light flux by the collimator lens 181. The split interference light LC forms an image on the image pick up surface of the CCD 184 by the image forming lens 183. The CCD 184 receives this interference light LC that is to be converted to an electrical detection signal, and outputs this detection signal to the arithmetic and control unit 200.

Constitution of Arithmetic and Control Unit

Next, referring to FIG. 4, FIG. 5, and FIG. 6, the configuration of the the arithmetic and control unit 200 is described. This arithmetic and control unit 200 analyzes the detection signal input from the CCD 184 of the spectrometer 180 of the OCT unit 150, and performs a process of forming tomographic images of a fundus oculi Ef of an eye E. The analysis technique then is the same technique as the conventional Fourier domain OCT technique.

Also, the arithmetic and control unit 200 operates to form a (image data of) 2-dimensional image showing the state of the surface of a fundus oculi Ef (retina) based on the video signal output from the imaging device 10 and 12 of the fundus camera unit 1A.

Furthermore, the arithmetic and control unit 200 executes the control of each part of the fundus camera unit 1A and the control of each part of the OCT unit 150.

Examples of control performed by the fundus camera unit 1A include emission of illumination light by the observation light source 101 or the imaging light source 103, the control of the photographic timing of the fundus oculi image by the imaging devices 10 and 12, the control of insertion/evacuation operations of the exciter filters 105 and 106 or the barrier filters 122 and 123 onto the optical path, the control of display operations of the LCD 140, the control of the aperture value of the photographing aperture 121, the movement control of the focusing lens 124 (the control of the focus adjustment operation and the control of the photographing magnification), the control of rotational operations of the Galvano mirrors 141A and 141B in the scanning unit 141, the emission of the first alignment light by the light source 110a of the first alignment optical system 110A, the control of insertion/evacuation operations of the alignment member 110 onto the optical path of the illuminating optical system 100, the emission of the second alignment by the light source 190a of the second alignment optical system 190A, and so on.

Whereas, as for the control of the OCT unit 150, emission of the low coherence light by a low coherence light source 160, control of accumulated time of the CCD 184, and movement control of reference mirror 174, etc. are to be performed.

The hardware configuration of the arithmetic and control unit 200 that acts as described above is explained referring to FIG. 4. The arithmetic and control unit 200 is provided with a hardware configuration that is the same as conventional computers. To be specific, the configuration includes: a microprocessor 201 (CPU, MPU, etc.), a RAM 202, a ROM 203, a hard disk drive (HDD) 204, a keyboard 205, a mouse 206, a display 207., an image forming board 208, and a communication interface (I/F) 209. Each part of these is connected through a bus 200a.

The microprocessor 201 executes operations characteristic to the present embodiment by loading a control program 204a that has been stored in the hard disk drive 204, on the RAM 202.

Furthermore, the microprocessor 201 executes control of each part of the device that has previously been described and various arithmetic processes, etc. Moreover, control of each part of the device that responds to an operation signal from the keyboard 205 or the mouse 206, control of display processes by the display 207, and control of transmitting/receiving processes of various types of data or control signals, etc. are executed by the communication interface 209.

The keyboard 205, the mouse 206 and the display 207 are used as a user interface of the fundus observation device 1. The keyboard 205 is used as a device for inputting letters or figures, etc. by typing. The mouse 206 is used as a device to perform various input operations with respect to the display screen of the display 207.

Furthermore, the display 207 as an arbitrary display device such as LCD (Liquid Crystal Display) or CRT (Cathode Ray Tube), etc. displays images of a fundus oculi Ef formed by the fundus observation device 1 and displays various operation screens or set up screens, etc, Furthermore, the user interface of the fundus observation device 1 is not limited to such a configuration but may be configured by using any user interfaces equipped with a function to display various information and a function to input various information such as track ball, control lever, touch panel type LCD, control panel for ophthalmology examinations.

An image forming board 208 is a dedicated electronic circuit for operating to form the image of the fundus oculi Ef of an eye E. In this image forming board 208, the fundus image forming board 208a and OCT image forming board 208b are installed. The fundus image forming board 208a is a dedicated electronic circuit for operating in order to form the image of the fundus oculi based on the video signal from the imaging device 10 or the imaging device 12 of the fundus camera unit 1A. Furthermore, the OCT image forming board 208b is a dedicated electronic circuit for operating in order to form fundus images (tomographic images) based on the detecting signal from CCD 184 of the spectrometer 180 in the OCT unit 150. The image forming board 208 allows the processing speed for forming fundus images to improve.

A communication interface 209 operates to send the control signal from a microprocessor 201 to the fundus camera unit 1A and OCT unit 150. Also, the communication interface 209 operates to receive the video signal from the imaging device 10 and 12 in the fundus camera unit 1A and the detecting signal from CCD 184 in the OCT unit 150, and it operates to input the signals to the image forming board 208. At this time, the communication interface 209 operates to input the video signal from the imaging device 10 and 12 to the fundus image forming board 208a, and it operates to input the detecting signal from CCD 184 to OCT image forming board 208b.

Moreover, when the arithmetic and control unit 200 is connected to a network such as LAN (Local Area Network) or Internet, etc., the communication interface 209 may be configured to be equipped with a network adopter such as LAN card, etc. or a communication equipment such as modem, etc. so as to be able to perform data communication through the network. In this case, a server accommodating the control program 204a may be installed, and at the same time, the arithmetic and control unit 200 may be configured as a client terminal of the server.

Control System Configuration

Then, the configuration of the control system of the fundus observation device 1 is explained with reference to FIG. 5 and FIG. 6. FIG. 5 shows the entire configuration of the control system and FIG. 6 shows the detailed configuration of a portion thereof. Incidentally, among the configurations that the fundus observation device 1 comprises, parts related to the operation or processes related to the present invention are particularly selected and described in FIG. 5 and FIG. 6.

The control system of the fundus observation device 1 is configured mainly having a controlling part 210 of the arithmetic and control unit 200. The controlling part 210 is comprised including: the microprocessor 201, the RAM 202, the ROM 203, the hard disk drive 204 (control program 204a), and the communication interface 209.

A controlling part 210 executes various control processes by a microprocessor 201 that runs based on a control program 204a. In particular, the controlling part 210 controls the detection timing of the reflection light by the fundus oculi Ef of the illumination light, or in other words, controls the radiographic timing of the fundus oculi image by the imaging devices 10, 12 of the fundus camera unit 1A. Similarly, the controlling part 210 controls the timing of the radiogram of the fundus oculi image by the CCD 184 of the spectrometer 180 on the OCT unit 150, or in other words, controls the timing of detection of the interference light LC.

The controlling part 210 comprises a main controller 210A, a detection timing controlling part 210B, and an alignment controlling part 210C, as shown in FIG. 6. The detection timing controlling part 210B acts as one example of the "detection timing controlling part" relating to the present invention. In addition, the alignment controlling part 210C acts as an example of the "controlling part" relating to the present invention.

The main controller 210A functions as a central unit of the controlling part 210 and controls the each part of the device. For example, the main controller 210A controls the display of two types of images obtained by the fundus observation device 1, that is, the two-dimensional image of the surface of the fundus oculi Ef by the fundus camera unit 1A (the fundus oculi image Ef) and the image of the fundus oculi Ef formed based on detection signals obtained by the OCT unit 150 (the tomographic image or the three-dimensional image) on the display part 240A (display 207) of the user interface 240. These fundus oculi images may be displayed on the display part 240A separately, or both images may be displayed side-by-side at the same time. In addition, the main controller 210A causes the display part 240A to display the scale S shown in FIG. 17 when the alignment bright points P1 and P2 are displayed on the display part 240A.

The detection timing controlling part 210B controls the timing of photographing the fundus oculi images by the fundus camera unit 1A or the OCT unit 150. Specifically, the detection timing controlling part 210B controls, for example, the frame rate of the imaging devices 10 and 12 or the CCD 184 by controlling the storage time of the image pick up element 10a, 12a and the CCD 184 and by controlling the electronic shutter similar as before.

In addition, the detection timing controlling part 210B controls the timing of power delivery to the observation light source 101, the imaging light source 103, and the low coherence light source 160 and thereby controls the emission timing of light by these light sources.

Particularly, the detection timing controlling part 210B controls the imaging light source 103 and the imaging device 10 (or the observation light source 101 and the imaging device 12) and the low coherence light source 160 and the CCD 184 respectively. Thereby, the detection timing controlling part 210B acts so as to synchronize the photographic timing of the two-dimensional image of the surface of the fundus oculi Ef and the photographic timing of the tomographic image of the fundus oculi Ef. At this time changes in orientation of Galvano mirrors 141A and 141B are synchronously controlled. The detection timing controlling part 210B controls the frame rate of the imaging device 10 (or imaging device 12) and the frame rate of the CCD 184. The ratio of the frame rates of the imaging device 10 (12) to the CCD 184 is adjusted to, for example, between 10:1 and 1:1.

In addition, the detection timing controlling part 210B controls the mirror drive mechanisms 241 and 242 of the fundus camera unit 1A respectively so as to operate each of the Galvano mirrors 141A and 141B independently and thereby controls scanning of the signal light LS. Furthermore, the detection timing controlling part 210B controls the reference mirror drive mechanism 243 and moves the reference mirror 174 in the direction of travel of the reference light LR (optical path direction).

The alignment controlling part 210C controls the timing of projecting the split indicators L1 and L2 onto the eye E by the first alignment optical system 110A, and controls the timing of projecting the alignment bright points P1 and P2 onto the eye E by the second alignment optical system 190A.

When projecting the split indicators L1 and L2, the alignment controlling part 210C inserts the inclined surface 110s of the alignment member 110 into the optical path by controlling the alignment drive mechanism 110g and illuminates the light source 110a. In addition, when terminating the projection of the split indicators, the alignment controlling part 210C evacuates the inclined surface 110s of the alignment member 110 from the optical path by controlling the alignment drive mechanism 110g and turns the light source 110a off. Incidentally, it is also allowed to configure so as to control the projection timing of the split indicators only by inserting and/or detaching the inclined surface 110s of the alignment member 110 onto the optical path. In addition, it is allowed to configure so as to control the timing of projecting the split indicators only by illuminating/turning off the light source 110a.

When projecting the alignment bright points P1 and P2, the alignment controlling part 210C illuminates the light source 190a. In addition, when terminating the projection of the alignment bright points P1 and P2, the alignment controlling part 210C turns the light source 190a off. Incidentally, it is also allowed to control the timing of projecting the alignment bright points P1 and P2 by configuring the half mirror 190 insertable and/or detachable to the optical path as well as the alignment member 110.

An image forming part 220 is intended to operate the process forming the fundus image based on the video signal from the imaging device 10 and 12 of the fundus camera unit 1A and to operate the process forming the fundus image based on the detecting signal from CCD 184 in the OCT unit 150. This image forming part 220 comprises an image formation board 208.

The image processing part 230 is used for various image processes to the fundus images formed by the image forming part 220. For example, it operates to form a 3-dimensional image of the fundus oculi Ef based on the tomographic images of the fundus oculi Ef corresponding to the detection signal from the OCT unit 150 and various corrections, such as brightness adjustment. This image processing part 230 may be comprised with the inclusion of a microprocessor 201, and may be comprised with the inclusion of an OCT image formation board 208b.

In addition, the image processing part 230 performs processes such as extracting layers in the tomographic image of the fundus oculi Ef (retina layer, choroid membrane, sclera, and so on), measuring the layer thickness, obtaining a distribution of layer thickness, and the calculating the difference in layer thickness.

The correction processing part 225 performs the process of correcting image positions of the tomographic images of fundus oculi Ef based on results of detecting interference light LC from the CCD 184 on the OCT unit 150 based on two-dimensional images of the surface of the fundus oculi Ef based on results of detecting the reflection light by fundus oculi Ef of the illumination light by the imaging device 10 (or imaging device 12) on the fundus camera unit 1A. This correction processing part 225 is equivalent to one example of "correction part" relating to the present invention and consists of the inclusion of a microprocessor 201 or the like.

The process of correcting the image positions of the tomographic images executed by the correction processing part 225 will now be described more specifically. An extraction processing part, which is not shown in any Figures, is built into the correction processing part 225. This extraction processing part analyzes the two-dimensional images of the surface of the fundus oculi Ef based on results of detection from the imaging device 10 (or imaging device 12) and extracts the characteristic part among these two-dimensional images. The characteristic parts subject to extraction are, for example, the optic papilla, macula lutea, a specific blood vessel or vascular bifurcation. The extraction processing part extracts the characteristic parts that are subject to extraction by analyzing the luminance and color of the two-dimensional images of the fundus oculi Ef, for example.

The correction processing part 225 acquires the image positions of the characteristic part extracted by the extraction processing part. These coordinate positions are expressed by a xy coordinate system shown, for example, in FIG. 1. In addition, the xy coordinate system is connected in advance to the two-dimensional coordinate system defined on the detection side of the image pick up element 10a (or imagine sensor element 12a of the imaging device 12) on the imagining device 10. The correction processing part 225 acquires the image positions of the relevant characteristic part by converting the image positions of the characteristic part expressed by the two-dimensional coordinate system on this detection surface to the image positions by means of the relevant xy coordinate system.

The correction processing part 225 corrects the image positions of the tomographic images of the fundus oculi Ef using the image positions of the characteristic part acquired in this way. Details of this correction process are described below.

The user interface (UI) 240 comprises a display part 240A consisting of display devices such as a display 207, and an operation part 240B consisting of operation devices or input devices such as a keyboard 205 and a mouse 206. Incidentally, the display part 240A may include any displaying part such as a touch panel monitor 11 provided on the fundus camera unit 1A. In addition, the operation part 240B may include any operating part such as a joystick 4, an operation button 4a, or other buttons or keys that are not shown.

The controlling feature of the scanning signal light LS by the controlling part 210 and the process feature to the detecting signal from the OCT unit 150 by the image forming part 220 and the image processing part 230 are respectively described below. Furthermore, an explanation regarding the process of the image forming part 220, etc., to the video signal from the fundus camera unit 1A is omitted because it is the same as the conventional process.

Regarding the Signal Light Scanning

Scanning of signal light LS is performed by changing the facing direction of the reflecting surfaces of the Galvano mirrors 141A and 141B of the scanning unit 141 in the fundus camera unit 1A. By controlling the mirror drive mechanisms 241 and 242 respectively, the controlling part 210 changes the facing direction of the reflecting surfaces of the Galvano mirror 141A and 141B, and scans the signal light LS on the fundus oculi Ef.

Once the facing direction of the reflecting surface of the Galvano mirror 141A is changed, the signal light LS is scanned in a horizontal direction (x-direction in FIG. 1) on the fundus oculi Ef. Whereas, once the facing direction of the reflecting surface of the Galvano mirror 141B is changed, the signal light LS is scanned in a vertical direction (y-direction in FIG. 1) on the fundus oculi Ef. Furthermore, by changing the facing direction of the reflecting surfaces of both Galvano mirrors 141A and 141B simultaneously, the signal light LS may be scanned in the composed direction of x-direction and y-direction. That is, by controlling these two Galvano mirrors 141A and 141B, the signal light LS may be scanned in an arbitrary direction on the xy plane.

Figure 7A:
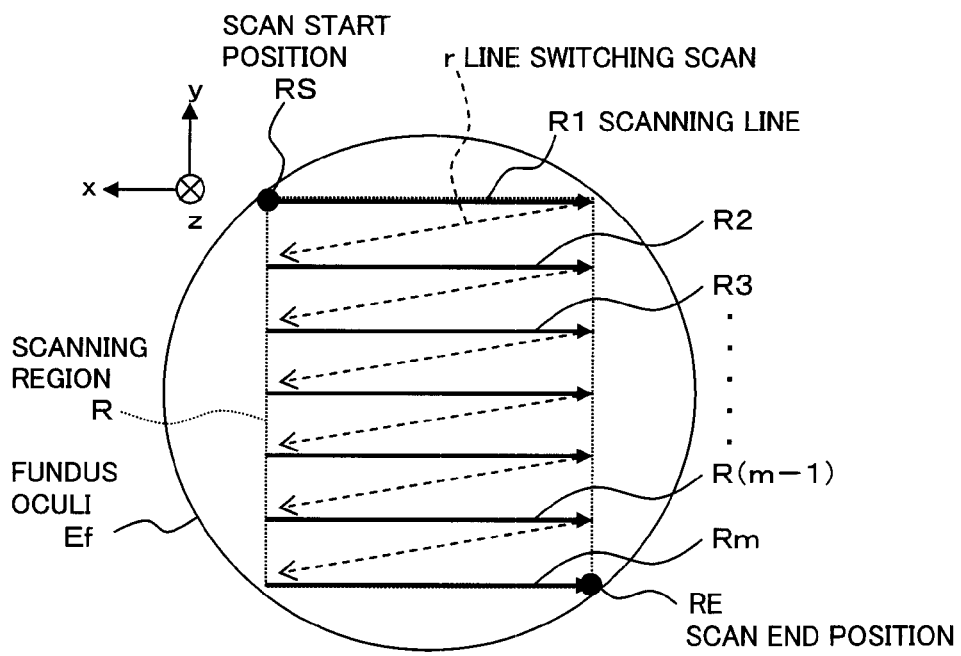
FIG. 7A represents one example of the scanning features of signal light when a fundus oculi is seen from the incident side of the signal light with respect to an eye. In addition.
Figure 7B:
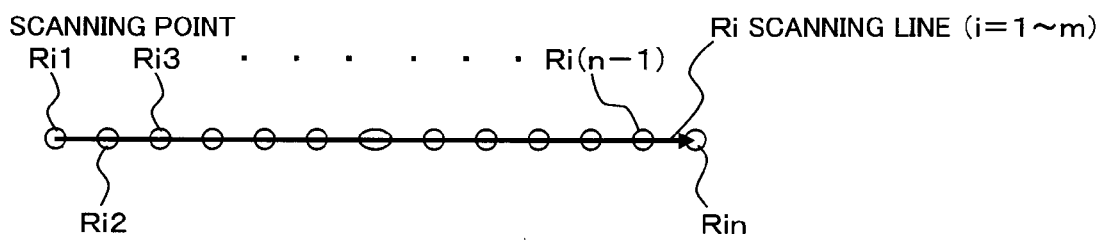
FIG. 7B represents one example of arrangement features of scanning points of each scanning line.

FIG. 7 represents one example of scanning features of signal light LS for forming images of a fundus oculi Ef. FIG. 7A represents one example of scanning features of the signal light LS, when the signal light LS sees the fundus oculi Ef from an incident direction onto the eye E (that is, +direction of z is seen from −direction of z in FIG. 1). Furthermore, FIG. 7B represents one example of arrangement features of scanning points (positions at which image measurement is carried out) on each scanning line on the fundus oculi Ef.

As shown in FIG. 7A, the signal light LS is scanned within a rectangular shaped scanning region R that has been preset. Within this scanning region R, plural (m number of) scanning lines R1 through Rm have been set in the x-direction. When the signal light LS is scanned along each scanning line Ri (i=1 through m), detection signals of interference light LC are to be generated.

Herein, the direction of each scanning line Ri is referred as the "main scanning direction" and the orthogonally crossing direction is referred as the "sub-scanning direction". Therefore, the scanning of the signal light LS in a main scanning direction is performed by changing the facing direction of the reflecting surface of the Galvano mirror 141A, and the scanning in a sub-scanning direction is performed by changing the facing direction of the reflecting surface of the Galvano mirror 141B.

On each scanning line Ri, as, shown in FIG. 7B, plural (n number of) scanning points Ri1 through Rin have been preset.

In order to execute the scanning shown in FIG. 7, the controlling part 210 controls the Galvano mirrors 141A and 141B to set the incident target of the signal light LS with respect to a fundus oculi Ef at a scan start position RS (scanning point R11) on the first scanning line R1. Subsequently, the controlling part 210 controls the low coherence light source 160 to flush the low coherence light L0 for emitting the signal light LS to the scan start position RS. The CCD 184 receives the interference light LC based on the fundus reflection light of this signal light LS at the scan start position RS, and outputs the detection signal to the controlling part 210.

Next, by controlling the Galvano mirror 141A the controlling part 210 scans the signal light LS in a main scanning direction and sets the incident target at a scanning point R12, triggering a flush emission of the low coherence light L0 for making the signal light LS incident onto the scanning point R12. The CCD 184 receives the interference light LC based on the fundus reflection light of this signal light LS at the scanning point R12, and then outputs the detection signal to the controlling part 210.

Likewise, the controlling part 210 obtains detection signals output from the CCD 184 responding to the interference light LC with respect to each scanning point, by flush emitting the low coherence light L0 at each scanning point while shifting the incident target of the signal light LS from scanning point R13, R14, . . . , R1 (n-1), R1n in order.

Once the measurement at the last scanning point R1n of the first scanning line RI is finished, the controlling part 210 controls the Galvano mirrors 141A and 141B simultaneously and shifts the incident target of the signal light LS to the first scanning point R21 of the second scanning line R2 following a line switching scan r. Then, by conducting the previously described measurement with regard to each scanning point R2j (j=1 through n) of this second scanning line R2, a detection signal corresponding to each scanning point R2j is obtained.

Likewise, by conducting a measurement with respect to the third scanning line R3, . . . , the m-1th scanning line R (m-1), the mth scanning line Rm respectively to obtain the detection signal corresponding to each scanning point. Furthermore, the symbol RE on a scanning line Rm is a scan end position in accordance with a scanning point Rmn.

As a result, the controlling part 210 obtains m×n number of detection signals corresponding to m×n number of scanning points Rij (i=1 through m, j=1 through n) within the scanning region R. Hereinafter, a detection signal corresponding to the scanning point Rij may be represented as Dij.

Such interlocking control of such shifting of scanning points and the emission of the low coherence light L0 may be realized by synchronizing, for instance, the transmitting timing of control signals with respect to the mirror drive mechanisms 241, 242 and the transmitting timing of control signals (output request signal) with respect to the low coherence light source 160.

As described, when each Galvano mirror 141A and 141B is being operated, the controlling part 210 stores the position of each scanning line Ri or the position of each scanning point Rij (coordinates on the xy coordinate system) as information indicating the content of the operation. This stored content (scan positional information) is used in an image forming process as was conducted conventionally.

Regarding Image Processing

Next, one example of the process relating to OCT images is described of the image forming part 220 and the image processing part 230. Only the process of forming tomographic images of the fundus oculi Ef and the process of forming three-dimensional images based on tomographic images are explained here, and the process of forming three-dimensional images including image position correction of tomographic images by the correction processing part 225 on the arithmetic and control unit 200 will be described later.

The image forming part 220 executes the formation process of tomographic images of a fundus oculi Ef along each scanning line Ri (main scanning direction). The image processing part 230 executes the formation process of a 3-dimensional image of the fundus oculi Ef based on these tomographic images formed by the image forming part 220.

The formation process of a tomographic image by the image forming part 220, as was conventionally done, includes a 2-step arithmetic process. In the first step of the arithmetic process, based on a detection signal Dij corresponding to each scanning point Rij, an image in the depth-wise direction (z-direction in FIG. 1) of a fundus oculi Ef at the scanning point Rij is formed.

Figure 8:
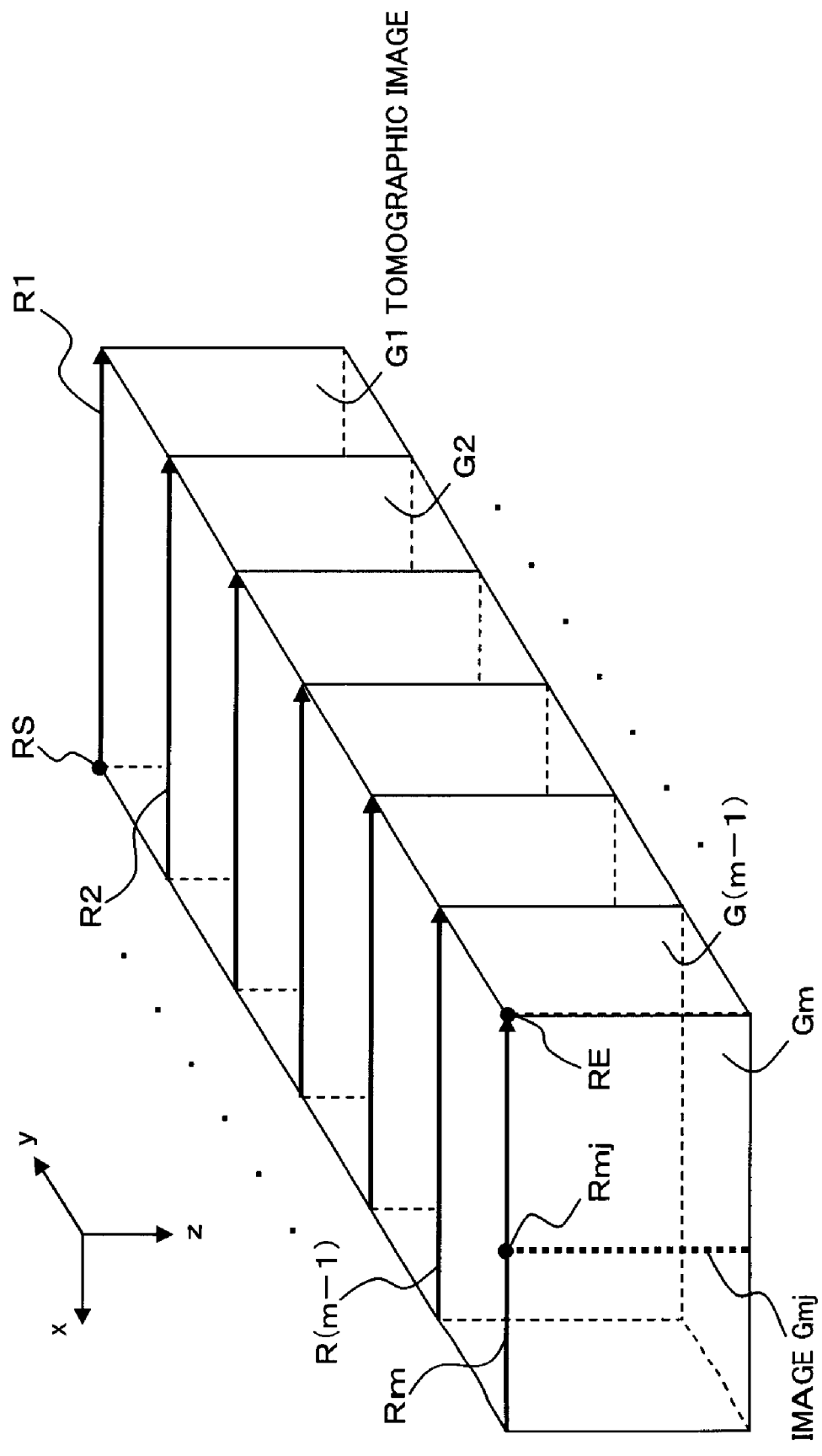
FIG. 8 is a schematic diagram representing one example of the scanning features of signal light and tomographic image features formed along each scanning line in an embodiment of the fundus observation device related to the present invention.

FIG. 8 represents a feature of a tomographic image formed by the image forming part 220. In the second step of the arithmetic process, with regard to each scanning line Ri, based on the images in the depth-wise direction at the n number of scanning points Ri1 through Rin thereon, a tomographic image Gi of a fundus oculi Ef along this scanning line Ri is formed. Then, the image forming part 220 determines the arrangement and the distance of each scanning point Ri1 through Rin while referring to the positional information (said scan positional information) of each scanning point Ri1 through Rin, and forms a tomographic image Gi along this scanning line Ri. Due to the above process, m number of tomographic images G1 through Gm at different positions of the sub-scanning direction (y-direction) are obtained.

Formation Process of 3-Dimensional Images

Next, the formation process of a 3-dimensional image of a fundus oculi Ef by the image processing part 230 is explained. A 3-dimensional image of a fundus oculi Ef is formed based on the m number of tomographic images (at least a plurality of tomographic images whereof) whose image positions have been corrected by the correction processing part 225. The image processing part 230 forms a 3-dimensional image of the fundus oculi Ef by performing a known interpolating process to interpolate an image between the adjacent tomographic images Gi and G (i+1).

Then, the image processing part 230 determines the arrangement and the distance of each scanning line Ri while referring to the positional information of each scanning line Ri to form this 3-dimensional image. For this 3-dimensional image, a 3-dimensional coordinate system (x,y,z) is set up, based on the positional information (said scan positional information) of each scanning point Rij and the z coordinate in the images of the depth-wise direction.

Furthermore, based on this 3-dimensional image, the image processing part 230 is capable of forming a tomographic image of the fundus oculi Ef at a cross-section in an arbitrary direction other than the main scanning direction (x-direction). Once the cross-section is designated, the image processing part 230 determines the position of each scanning point (and/or an image in the depth-wise direction that has been interpolated) on this designated cross-section, and extracts an image (and/or image in the depth-wise direction that has been interpolated) in the depth-wise direction at each determined position to form a tomographic image of the fundus oculi Ef at the designated cross-section by arranging plural extracted images in the depth-wise direction.

Furthermore, the image Gmj in FIG. 8 represents an image in the depth-wise direction (z-direction) at the scanning point Rmj on the scanning line Rm. Likewise, an image in the depth-wise direction at each scanning point Rij on the scanning line Ri formed by the arithmetic process of said first step may be represented as "image Gij."

In addition, the process of forming three-dimensional images of fundus oculi Ef described here is assumed to be when m number of tomographic images G1-Gm are displaced in the xy direction, or in other words, when eye movement of the eye subject to examination E occurs during image measurement of the tomographic images G1-Gm. The following [Operation] section describes operation of the fundus observation device 1 for optimally forming three-dimensional images even if eye movement of the eye subject to examination E occurs during image measurement of the tomographic images G1-Gm.

Operation

Figure 9:
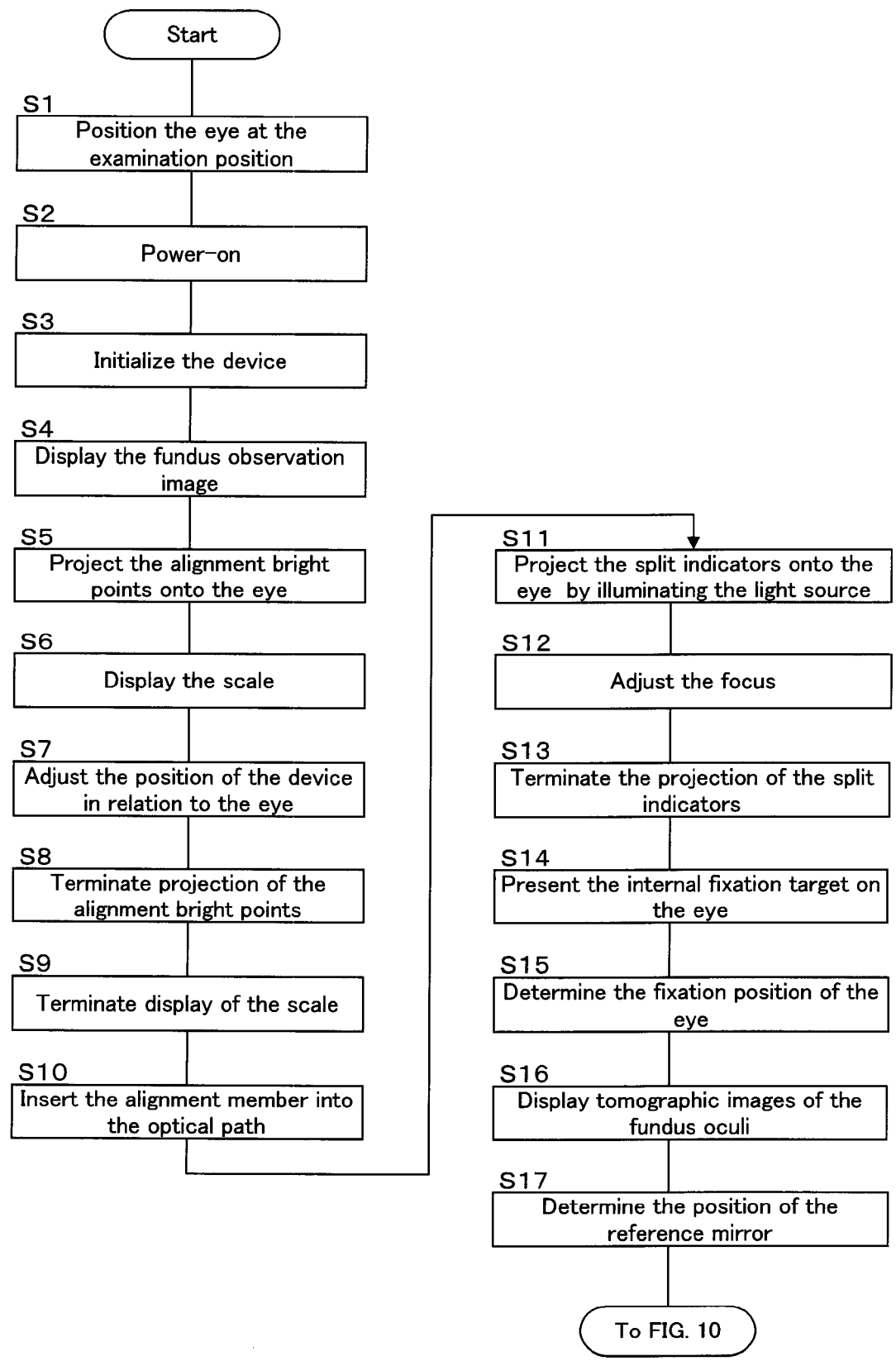
FIG. 9 is a flow chart showing one example of the procedure for operation of forming three-dimensional images of fundus oculi by means of an embodiment of the fundus observation device related to the present invention.
Figure 10:
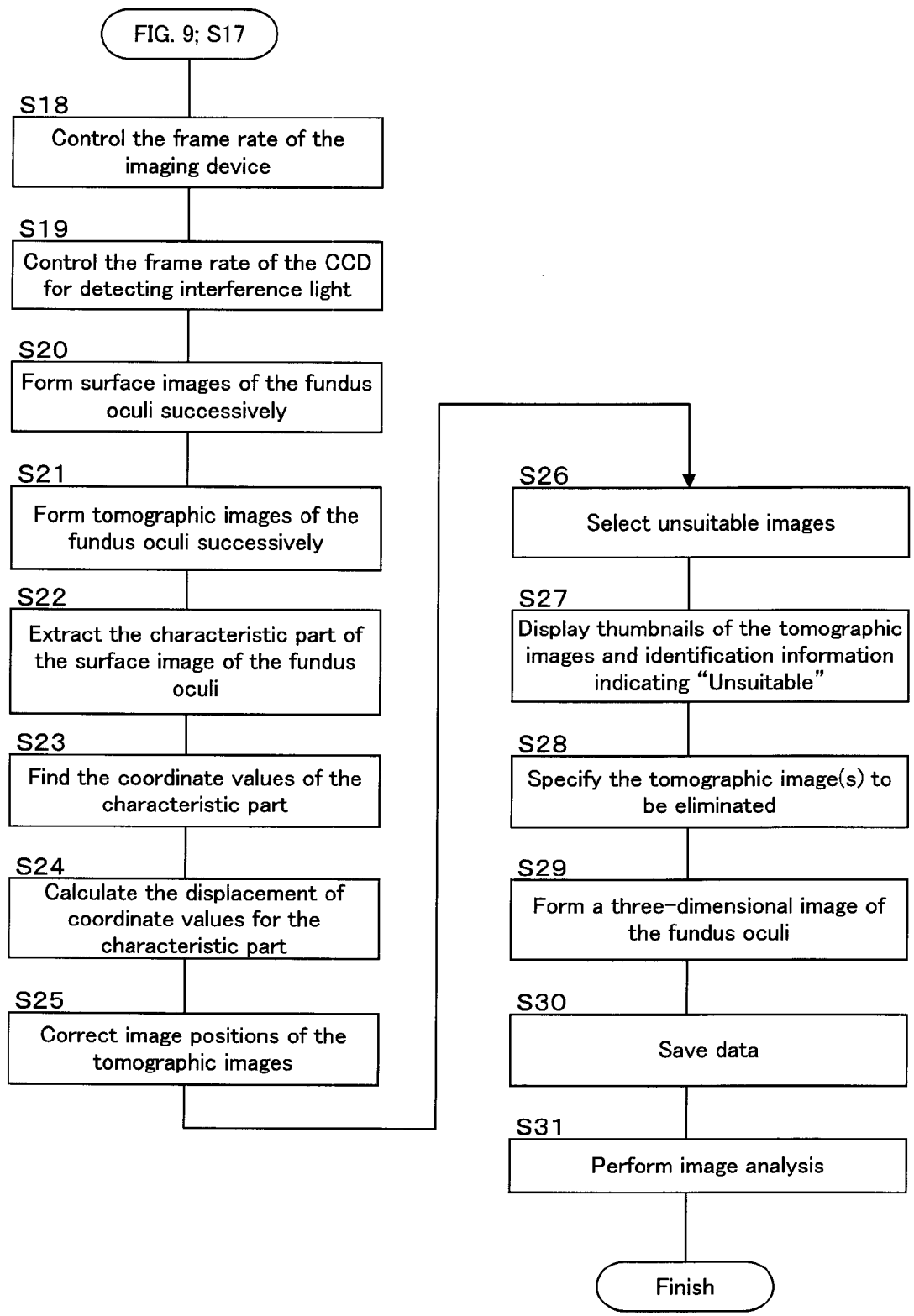
FIG. 10 is a flow chart showing one example of the operation of forming three-dimensional images of fundus oculi by means of an embodiment of the fundus observation device related to the present invention.

Next, operations of the fundus observation device 1 related to the present embodiment are described. The flowchart shown in FIG. 9 and FIG. 10 shows an example of procedure of the fundus observation device 1. FIG. 11 is a schematic diagram of this image position correction process.

Also described is the case in which the ratio of the frame rate of the fundus camera unit 1A (imaging device 10 and/or 12.) to the frame rate of the OCT unit 150 (CCD 184) is 2:1. However, even when the ratio of these frame rates is other than 2:1, it is possible for a similar process to be executed.

At Power-On; Steps S1 to S4

First, an examiner arranges an eye E at the predetermined examination position by mounting a subject's jaw on a jaw holder 6 (S1), and powers on the fundus observation device 1 by operating a power switch or the like not shown (S2).

The main controller 210A initializes the device in response to the power-on (S3). This initialization may be processes of clearing the memory (RAM 202 in FIG. 4) and moving the movable optical devices such as the Galvano mirrors 141A/141B and the reference mirror 174 to predetermined initial positions. Incidentally, it is also possible to configure to move these optical devices to the initial position corresponding to an eye E with reference to information related to that eye.

Next, the detection timing controlling part 210B controls the observation light source 101 and the imaging device 12 and photographs the image of the surface of the fundus oculi Ef. The main controller 210A causes the display part 240A to display this photographic image (fundus oculi observation image) (S4).

Alignment and Focus Adjustment: Steps S5 to S13

Then, the position (alignment) and focus for an eye E are adjusted. For that purpose, first, the alignment controlling part 210C illuminates the light source 190a of the second alignment optical system 190A and projects the alignment bright points P1 and P2 onto the eye E (S5). In addition, the main controller 210A causes the display part 240A to display the scale S of FIG. 17 (S6). Thus, the fundus observation image, the alignment bright points P1 and P2, and the scale S are displayed on the display part 240A at the same time.

The examiner adjusts the position of the device to the eye E by operating the joystick 4 shown in FIG. 1 and adjusting the position of the device such that the alignment bright points P1 and P2 are within the scale S (S7).

When the position adjustment of the device terminates, the alignment controlling part 210C turns the light source 190a off and terminates the projection of the alignment bright points P1 and P2 onto the eye E (S8), and the main controller 210A terminates the display of the scale S (S9).

Incidentally, it is possible to configure the termination of the position adjustment to be detected based on the manual operation or to be detected automatically. As one example of the configuration to be operated manually, the termination of the position adjustment is detected by configuring such that the examiner performs a predetermined operation (such as pressing the operation button 4a on the top of the joystick 4) when terminating the position adjustment. On the contrary, one example of the configuration for automatic operation is as follows. At first, the pixel value (luminance value) on the display screen is analyzed to detect the coordinates (display position) of the alignment bright points P1 and P2. Then, it is determined whether they are within the scale S. Finally, the termination of the position adjustment is detected when it is determined that they are within the scale S. Herein, it may configure to determine that the position adjustment terminates when positions of the alignment bright points P1 and P2 have not moved for a predetermined period.

Next, while the alignment controlling part 210 inserts the alignment member 110 into the optical path by controlling the alignment drive mechanism 110g (S10), the alignment controlling part 210 projects the split indicators L1 and L2 onto the eye E by illuminating the light source 110a of the first alignment optical system 110A (S11). As a result, a fundus observation image and the split indicators L1 and L2 are displayed on the display part 240A.

The examiner operates the focusing knob described above to adjust the focus such that the lateral positions of the split indicators L1 and L2 are coincident with each other (S12). When the focus adjustment terminates, the alignment controlling part 210C turns off the light source 1110a and evacuates the alignment member 110 from the optical path so as to terminate the projection of the split indicators L1 and L2 onto the eye E (S13).

Fixation Position Adjustment; Steps S14 and S15

Then, the eye E is fixated in the predetermined direction in order to observe the region of interest of the fundus oculi Ef. For that purpose, the main controller 210A by controls the LCD 140 to display an internal fixation target that is not shown. As a result, the internal fixation target is presented on the eye E (S14). This internal fixation target is, for example, a target (such as a bright point) displayed on the LCD 140, and acts so as to guide the eye-gaze direction of the eye E by changing its display position.

The examiner operates the focusing operation part 240B and determines the present position of the internal fixation target, that is, the fixation position of the eye E so that the image of the region for observation in the fundus oculi Ef is displayed on the display part 240A (S15). The main controller 210A causes the display part 240A to display the information regarding the determined fixation position.

Interference Position Adjustment; Steps S16 and S17

Next, the position of the reference mirror 174 during capturing a cross-sectional image is determined. For that purpose, the detection timing controlling part 210B moves the reference mirror 174 by controlling the reference mirror drive mechanism 243, changes the orientations of the Galvano mirrors 141A and 141B by controlling the mirror drive mechanisms 241A and 241B, and has the CCD 184 to detect the interference light LC at the predetermined frame rate (e.g., at approximately 5 to 15 (frame/second)) by having the low coherence light source 160 to emit the low coherence light LO.

At this time, the timing of change in orientation of the Galvano mirrors 141A and 141B, the emission timing of the low coherence light LO, and the detection timing of the interference LC by the CCD 184 are synchronized with each other. In addition, movement of the reference mirror 174 may be controlled based on the manual operation by the examiner or may be performed automatically.

The main controller 210A causes the display part 240A to displays the tomographic image of the fundus oculi Ef at that frame rate based on the detection signals input from the CCD 184 (S16). As a result, the fundus oculi observation image and the tomographic image are displayed on the display part 240A.

The examiner determines the position of the reference mirror 174 such that the tomographic image is in the desired display state (such as the desired depth (z position) and the precision of the image) (S17). At this time, if required, the orientations of the polarizing axes of the low coherence light LO, the signal light LS, the reference light LR, and the interference light LC are corrected. Consequently, the preparation for capturing a tomographic image of the fundus oculi Ef is completed. The operation for capturing the tomographic image is explained below.

Detection of Low Coherence Light LO; Steps S18, S19

When the predetermined operation for starting to capture the tomographic image (e.g. putting down the operation button 4a etc) is instructed, the detection timing controlling part 210B illuminates the observation light source 101 and controls the imaging device 12 so as to detect the reflection light by the fundus oculi Ef of the illumination light from the observation light source 101 by the frame rate f1 (first/second) (S18), and then controls low coherence light source 160 and the CCD 184 and cause CCD 184 to-detect the interference light LC by the frame rate f2 (frames/second) (S119). At this time, the frame rate f1 of the imaging device 12 and the frame rate f2 of the OCT unit 150 are mutually synchronized by the detection timing controlling part 210B.

Surface Images, Formation of Tomographic Images: Steps S20, S21

The image forming part 220 sequentially forms surface images of the fundus oculi based on image signals sequentially output from the imaging device 12 (S20), and sequentially forms tomographic images of fundus oculi Ef based on detection signals input sequentially from the CCD 184 (S21).

FIG. 11 shows one example of the formation of surface images and tomographic images of the fundus oculi Ef formed in steps S20 and S21. FIG. 11 shows surface images and tomographic images of the fundus oculi Ef sequentially formed by the image forming part 220 when the ratio of the frame rate f1 of the imaging device 12 to the frame rate of the CCD 184 is f1:f2=2:1.

FIG. 11A, FIG. 11B, FIG. 11C, and FIG. 11D show the image formed based on the interference light LC and the reflection light by the fundus oculi Ef of the illumination light detected at times t=t1, t2, t3, and t4, respectively. In addition, these images show only some of the images formed in the serial process of forming images. Furthermore, the intervals of detection times t(k+1)−tk (k=1, 2, 3, ... )=Δt are constant.

Figure 11A:
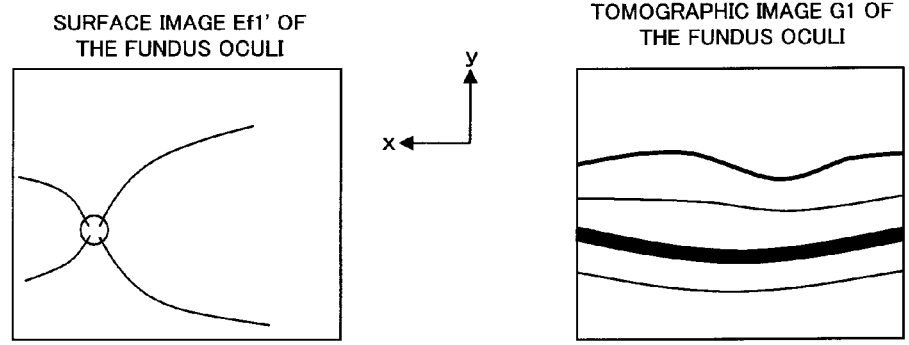
FIG. 11 is a schematic diagram of process for correcting the image position of tomographic images of the fundus oculi according to an embodiment of the fundus observation device related to the present invention.

In time t=t1, both the imaging device 12 and the CCD 184 are controlled so as to detect light, and the surface image Ef1' and the tomographic image G1 of the fundus oculi Ef (See FIG. 7 and FIG. 8;) are formed based on each of the detected results (See FIG. 11A).

Figure 11B:
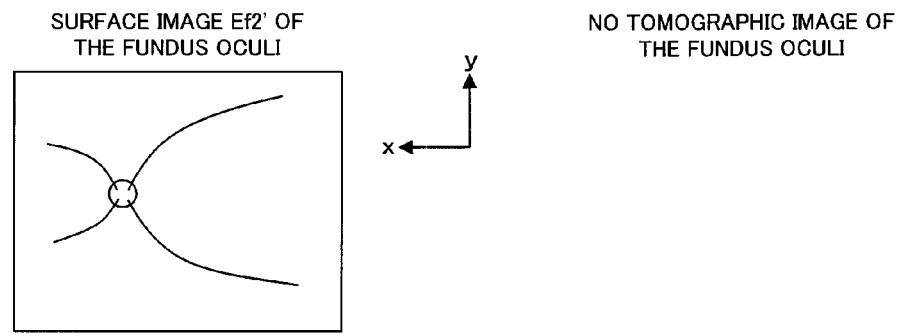

In time t=t2, only the imaging device 12 is controlled so as to detect light, and the surface image Ef2' of the fundus oculi Ef is formed based on these detected results (See FIG. 11B).

Figure 11C:
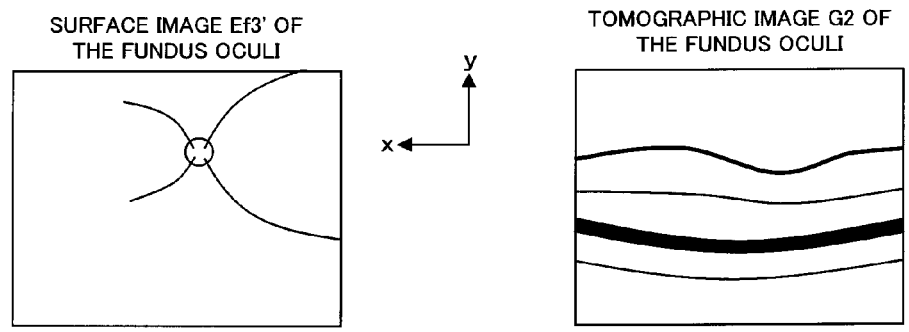

In time t=t3, both the imaging device 12 and the CCD 184 are controlled so as to detect light similar to the case with time t=t1, and based on each of the detected results, the surface image Ef3' and the tomographic images G2 of the fundus oculi Ef (See FIG. 7 and FIG. 8) are formed (See FIG. 11C).

Figure 11D:
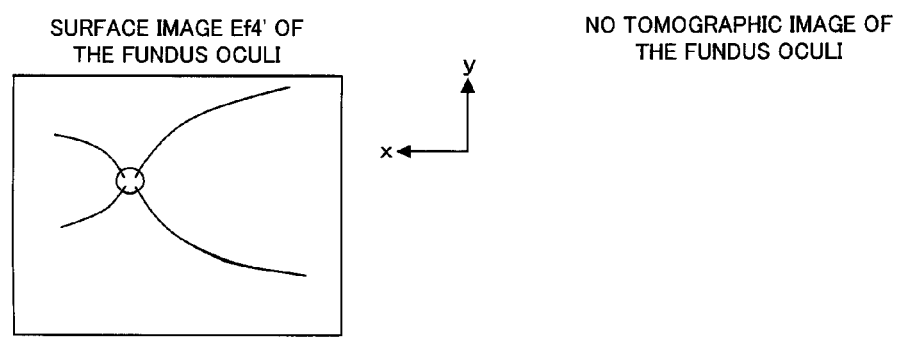

In time t=t4, only the imaging device 12 is controlled so as to detect light similar to the case with time t2, and the surface image Ef4' of the fundus oculi Ef is formed based on the detected results (See FIG. 11D).

Below, fundus oculi images are similarly formed for t=t5, t6, t7, etc. In other words, when the ratio of the frame rate f1 of the imaging device 12 to the frame rate f2 of the CCD 184 is 2:1, both the imaging device 12 and the CCD 184 detect light at time t=tk (k=odd number), and a surface image Efk' and tomographic image G((k+1)/2) of the fundus oculi Ef are acquired, and only the imaging device 12 detects light at time t=tk (k=even number) and only the surface image Efk' on the locus oculi Ef is acquired.

The surface images Ef1'-Ef4' of the fundus oculi Ef shown in FIG. 11 differ in the positions of the images of optic papilla and blood vessels among the frames. This indicates the occurrence of eye movement of the eye E during the examination. Described below is the process for forming three-dimensional images under such circumstances.

Image Position Correction for Tomographic Images: Steps S22-S25

The extraction processing part (previously described) of the correction processing part 225 extracts the characteristic part of each surface image produced at the same time as the tomographic images (S22). In the example shown in FIG. 11, the correction processing part 225 analyzes each of the surface images Efk' (k=odd number) and extracts the image area corresponding to the optic papilla in the fundus oculi Ef by extracting the image area of an approximate round shape having a roughly equal luminance value.

The correction processing part 225 finds the coordinate values of the extracted characteristic part (S23). As an example of this process, the correction processing part 225 determines the coordinate values (x coordinate, y coordinate) of predetermined positions in the image areas of the extracted optic papilla extracted in Step S22, such as the coordinate values of pixels having the greatest luminance value.

Next, the correction processing part 225 calculates the displacement of coordinate values for the characteristic part obtained from another surface image Efk' (k=odd number) for coordinate values of a characteristic part obtained from one of the surface images Efk' (k=odd number) (S24). For example, displacement ($\Delta$ xk=xk−x1, $\Delta$ yk=yk−y1) of the coordinate values (xk, yk) of the characteristic part of each surface image Efk' (k=3, 5, 7, etc.) is calculated for the coordinate values (x1, y1) of the characteristic part of the surface image Ef1'. In other words, the correction processing part 225 calculates the relative displacement of image positions of a plurality of extracted characteristic parts.

Furthermore, the correction processing part 225 corrects image positions of the tomographic images using the displacement of the coordinate values of the characteristic part calculated in Step S24 (S25). In the example mentioned above, for each of k=3, 5, 7, etc. (odd numbers), the image position of the tomographic image G((k+1)/2) is moved by (−$\Delta$ xk, −$\Delta$ yk), correcting it so as to match the image position of the tomographic image G1.

Formation of Three-Dimensional Images: Step S26-S29

Then, a three-dimensional image of the fundus oculi Ef is formed. For that purpose, among a plurality of tomographic images in which the image position has been corrected, the image processing part 230 selects the inappropriate images such as those that have been captured when the eye E blinked and those whose misalignment of the image position is larger than the predetermined value (S26). Such selection can be accomplished by analyzing the pixel value of the tomographic image or by basing on the correction amount of the image position. Incidentally, it is also possible to employ the conventional way of blink detection.

The main controller 210A causes the display part 240A to display thumbnails of plurality of tomographic images side-by-side and to display the identification information enabling to identify the tomographic image selected at the step S26 (S27). This identification in-formation may be a mark showing an inappropriate tomographic image (e.g., "x") or a list of inappropriate tomographic images.

The examiner operates the operation part 240B with reference to the identification information so as to specify the tomographic image to be eliminated from formation of a three-dimensional image (S28).

The image processing part 230 forms a three-dimensional image of the fundus oculi Ef based on the tomographic images not specified at the step S28 (S29). Consequently, formation of a three-dimensional image of the fundus oculi Ef by the fundus observation device 1 is completed.

Saving Data: Step S30

When capturing a tomographic image or a three-dimensional image of the fundus oculi Ef terminated, the main controller 210A stores the image data of these images and the images of the surface of the fundus oculi Ef (fundus oculi photographing image) in the hard disk drive 204 or an external memory device (such as database) (S30). Incidentally, the fundus oculi photographing image may be an image photographed by the imaging device 10 by illuminating the imaging light source 103, for example, immediately after capturing the tomographic image (step S21). Incidentally, it is preferable to configure so as to save the patient information such as name of subjects and patient ID and the associated information during capturing images (e.g., examination date and time, fixation position, interference position, and so on) with the image data of the image of the fundus oculi Ef.

Image Analysis: Step S31

An examiner (doctor) reads, out the saved images of the fundus oculi Ef by performing the predetermined operation, and has the image processing part 230 to analyze the image such as extracting layers in a tomographic image of the fundus oculi Ef, measuring the thickness of the layers, creating a distributed image of the layer thickness, calculating the difference of layer thickness, and creating images of any cross-section of a three-dimensional image depending on the diagnostic purpose (S31). Then, that eye is diagnosed with reference to the result of such analysis.

Effect and Advantage

The operation and effect of the fundus observation device 1 related to the present embodiment having the constitution as above is explained.

This fundus observation device 1 comprises the fundus camera unit 1A for operating as the fundus camera in order to capture 2-dimensional images showing the state of the surface of the fundus oculi Ef and the OCT unit 150 for operating as an optical image measuring device in order to capture tomographic images (and 3-dimensional images) of the fundus oculi Ef.

The optical path of the signal light used for image forming by the OCT unit 150 is guided to an eye E by combining the optical path (the imaging optical path) for forming by the imaging optical system 120 of the fundus camera unit 1A. The combining of this optical path is performed by the dichroic mirror 134.

In addition, the fundus reflection light of the signal light LS is guided to the dichroic mirror 134 along the imaging path, and goes to the OCT unit 150 by being separated from the imaging optical path via this dichroic mirror 134.

As a result, by setting the dichroic mirror 134 for operating in order to combine and separate the imaging optical path of the fundus camera unit 1A and the optical path of the signal light LS, it is possible to capture both 2-dimensional images of the surface of the fundus oculi Ef and tomographic images of the fundus oculi Ef (and 3-dimensional images).

In particular, to an eye E, if illumination of the illumination light by the fundus camera unit 1A and illumination of the signal light LS by the OCT unit 150 are simultaneously operated, each fundus reflection light can be separated via the dichroic mirror 134 and images formed by detecting each of them, making it possible to simultaneously produce both 2-dimensional images of the surface of the fundus oculi Ef and tomographic images of the fundus oculi Ef.

At this time, the signal light LS from the OCT unit 150 and the simultaneously illumination light may be near-infrared light from the imaging light source 103 and also visible light from the observation light source 101.

In addition, according to the fundus observation device 1 related to the present embodiment, it is configured to capture a tomographic image or a surface image of the fundus oculi Ef after automatically terminating the projection of the alignment bright points P1 and P2 or the split indicators L1 and L2 (alignment indicators) onto the eye E, and therefore it is possible to prevent the alignment indicators from being reflected in the image of the fundus oculi Ef.

Particularly, the image position can be corrected adequately because it is possible to prevent alignment indicators from being reflected in the image of the surface of the fundus oculi (fundus oculi observation image) for correcting the position of tomographic images of the fundus oculi. Therefore, even if the eye subject to examination E moves while measuring the tomographic images of the fundus oculi Ef, the image positions of the tomographic images can be corrected using the surface images of the fundus oculi Ef produced at the same time as detecting the interference light LC that forms the base of the tomographic images, and it is possible to form highly reliable three-dimensional images based on the tomographic images for which the image positions have been corrected.

Incidentally, in the present embodiment, it is configured to terminate the projection of the alignment indicators immediately after the termination of the alignment and focus adjustment, but the timing of the termination of the projection is not limited to this. In other words, the Liming of the termination of projecting the alignment indicators can be at any timing between immediately after the termination of the alignment or the like and immediately before the image capturing of the fundus oculi Ef (step S18).

In addition, when applying the configuration in which plurality of kinds of alignment indicator can be projected as the present embodiment, the projection of each alignment indicator can be terminated individually, or the projection of two or more kinds of alignment indicators can be terminated at the same time.

In addition, the fundus observation device 1 of the present embodiment is configured to be capable of projecting both the alignment bright points P1 and P2 and the split indicators L1 and L2 onto an eye E, but it is also possible to configure it to project only one of them (that is, the configuration can be provided with just one of the first alignment optical system 110A and the second alignment optical system 190A.).

As an example, the timing of terminating the projection of alignment indicators can be immediately after the presentation of the internal fixation target (step S14), immediately after the determination of the fixation position (step S15), immediately after the displaying of the tomographic image of the fundus oculi Ef (step S16), immediately after the determination of the position of the reference mirror 174 (S17), and so on. However, it is preferable to terminate the projection immediately after the termination of the alignment or immediately after the termination of the focus adjustment in order to obtain an advantage to be explained next.

In other words, since the fundus observation device 1 is configured to adjust the fixation position or the position determination of the reference mirror 174 after automatically terminating projection of the alignment indicators, the tasks of fixation position adjustment or reference mirror position determination can be easily and adequately accomplished without alignment indicators being reflected in the fundus observation image or the tomographic image.

Incidentally, in the present embodiment, both alignment bright points P1 and P2 for position adjustment of the device in relation to an eye E and the split indicators for focus adjustment are employed, but it is also possible to adopt a configuration in which only one of these is employed. In addition, it is also possible to use alignment indicators of any feature other than these. In that case, the similar advantage on the present embodiment can be obtained by a configuration to terminate the projection of that alignment indicator onto the eye E at any timing between immediately after using that alignment indicator and image capturing of the fundus oculi Ef, and more preferably, immediately after using that alignment indicator.

MODIFIED EXAMPLE

The constitution described above is merely one example to preferably implement the fundus observation device related to the present invention. Therefore, optional modifications may be implemented appropriately within the scope of the present invention.

Figure 12:
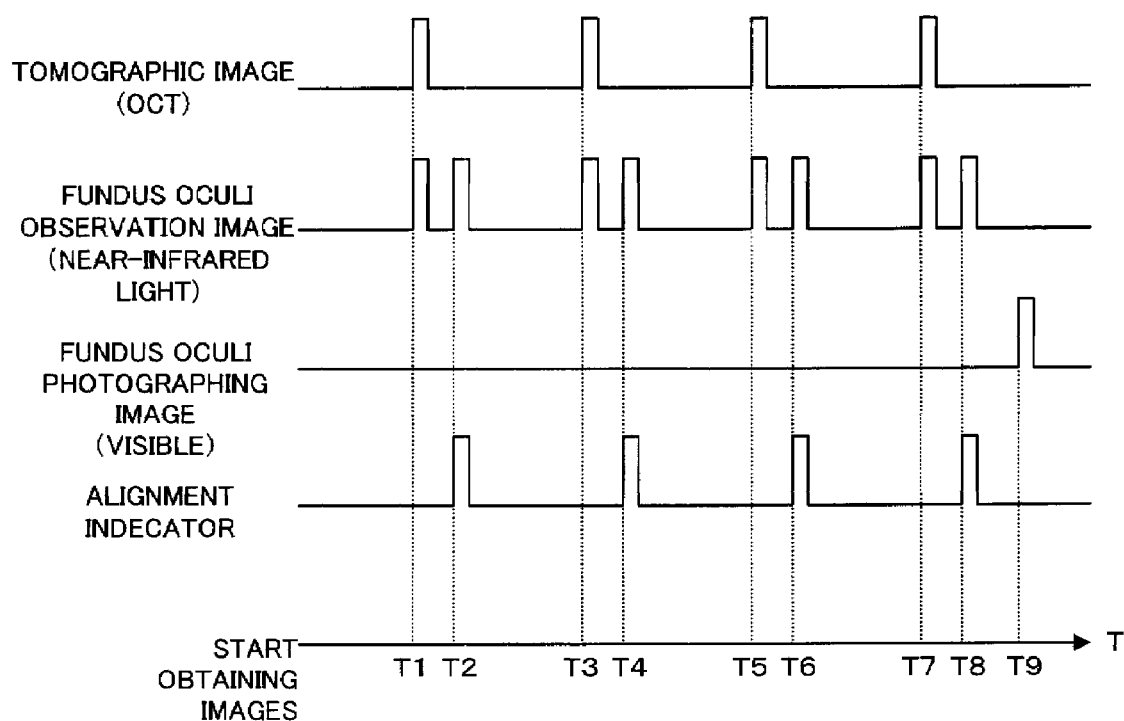
FIG. 12 is a view of an example of the operation timing of a modified example of an embodiment of the fundus observation device related to the present invention.

FIG. 12 shows an example of the operation timing of the fundus observation device related to the present invention. FIG. 12 describes the capture timing of tomographic images by the OCT unit 150, the capture timing of fundus oculi observation images by the observation light source 101 and the imaging device 12, the capture timing of fundus oculi photographing images by the imaging light source 103 and the imaging device 10, and the projection timing of alignment indicators onto an eye E.

Incidentally, the detection timing controlling part 210B controls the capture timing of images and the alignment controlling part 210C controls the projection timing of alignment indicators. In addition, linkage (synchronization) between the capture timing of images and the projection timing of alignment indicators is performed by the main controller 210A.

In addition, the alignment bright points P1 and P2 shall be projected onto the eye E as alignment indicators. The main controller 210A may cause to display the scale S when projecting the alignment bright points P1 and P2.

FIG. 12 describes the case of capturing four tomographic images, but the number of tomographic images to be captured is arbitrary.

When the instruction or capturing tomographic images of the fundus oculi Ef is operated, first, at time T=T1, tomographic images of the fundus oculi Ef (tomographic image G1 of FIG. 8) and the fundus oculi observation image G1' are captured.

Next, at time T=T2, the alignment bright points P1 and P2 are projected onto the eye E and the fundus oculi observation image G2' is captured.

Next, at time T=T3, the tomographic image G2 of the fundus oculi Ef and the fundus oculi observation image G3' are captured.

Next, at time T=T4, the alignment bright points P1 and P2 are projected onto the eye E and the fundus oculi observation image G4' is captured.

Next, at time T=T5, the tomographic image G3 of the fundus oculi Ef and the fundus oculi observation image G5' are captured.

Next, at time T=T6, the alignment bright points P1 and P2 are projected onto the eye E and the fundus oculi observation image G6' is captured.

Next, at time T=T7, the tomographic image G4 of the fundus oculi Ef and the fundus oculi observation image G7' are captured.

Next, at time T=T8, the alignment bright points P1 and P2 are projected onto the eye E and the fundus oculi observation image G8' is captured.

Finally, at time T=T9, the fundus oculi observation image G' is captured.

The correction processing unit 225 corrects the image positions of each tomographic image G1, G2, G3, and G4 based on the fundus oculi observation images G1', G3', G5', and G7' captured at the same time with them, respectively. In this way, the correction precision can be improved by correcting the image position of tomographic images by using the fundus oculi observation images captured at the same time, thereby forming three-dimensional images with high degree of certainty.

The alignment bright points P1 and P2 are respectively reflected into the fundus oculi observation images (12', G4', G6', and G8' captured immediately after capturing each tomographic image G1, G2, G3, and G4. Each fundus oculi observation image G2', G4', G6', and G8' is captured during the line change scanning r shown in FIG. 7. The main controller 210A causes the display part 240A to display the fundus oculi observation images G2', G4', G6', and G8' and the scale S when the tomographic images G1, G2, G3, and G4, for example, are displayed after capturing images or the like (e.g., during the image analysis at step S31 of FIG. 11).

Incidentally, it is also possible to configure to project the alignment bright points P1 and P2 and capture the fundus oculi observation images immediately before capturing each tomographic image G1 to G4. Herein, the time interval between the time of capturing the tomographic image and the time of capturing the fundus oculi observation image into which the alignment bright points P1 and P2 are reflected (T2-T1 or the like) corresponds to one example of the "predetermined time" relating to the present invention.

An examiner can have visual contact with the positional relationship between the scale S and the alignment bright points P1 and P2 in the fundus oculi observation image G6', so as to determine whether the position of an eye E is out of alignment when the tomographic image G3 has been captured.

The fundus oculi photographing image G' can also be photographed before or during capturing tomographic images, but it is preferred to be photographed in the end as described above because the pupil of the eye E might become miotic due to the projection of the flush light form the imaging light source 103. This fundus oculi photographing image G' is saved with tomographic images G1 to G4 and used as diagnostic material.

The embodiment mentioned above is comprised so as to correct the image positions of the tomographic images using the surface images of the fundus oculi Ef produced while detecting interference light LC that forms the base of the tomographic images, but it is not limited to this. For example, if the degree of discrepancy between the time when the interference light LC is detected and the time when the surface images are produced can be ignored regarding movement of the eye subject to examination E, it is possible to compose the embodiment so as to correct the image positions of the relevant tomographic images using the relevant surface images.

For example, as shown in FIG. 11, it is possible to correct the image positions of the relevant tomographic images using surface images produced with frames before and after the relevant tomographic images such as correcting the image positions of a tomographic image G2 using the surface image Ef4'.

Furthermore, it is not necessary for the timing of obtaining the surface images of fundus oculi Ef and the timing of detecting the interference light LC to always coincide. For example, it is allowable for the difference in timing of movement of the eye subject to examination E to be an ignorable degree. Such difference of timing within the accepted range is referred to as "substantially simultaneous" in the present embodiment. However, it is possible to improve the precision of correction of the tomographic images based on the relevant interference light LC by simultaneously obtaining the surface images and detecting the interference light LC as in the embodiment mentioned above.

Furthermore, in the embodiment mentioned above, the ratio of the frame rate of the fundus camera unit 1A and the frame rate of the OCT unit 150 is set to about 1:1 to 10:1, but it is not limited to this range. However, in order to secure surface images for correction of image positions of all of tomographic images, it is preferable to set the frame rate of the fundus camera unit 1A above the frame rate of the OCT unit 150. In particular, by setting the ratio of frame rates at 1:1, it is possible to perform an effective and efficient correction process by synchronizing the timing of imaging surface images with the timing of detecting the interference light LC.

Incidentally, in the above embodiment, the photographic timing of the surface image of the fundus oculi Ef and the detection timing of the interference light LC are synchronized, but the present invention is not limited to this. For example, it may be configured to save surface images of plurality of the fundus oculi Ef captured successively at the frame rate of the imaging devices 12a on the side of the fundus camera unit 1A into a memory device such as a memory together with its capturing time and to save the detection data of the interference light LC by the CCD 184 into the memory device together with the detection timing (detection time). Then, it is possible to configure the detecting data of each interference light LC to correct tomographic images based on that interference light LC by reading the surface image of the capturing time corresponding to the detection timing. Herein, as the "surface image of the capturing time corresponding to the detection timing of the interference light LC," it is possible, for example, to select the surface image of the capturing time that is closest to the detection timing among a plurality of the surface images of fundus oculi Ef. This modified example is not configured to directly synchronize the photographic timing of the surface image with the detection timing of the interference light LC, but a similar advantage on the above embodiment can be obtained because the tomographic image can be corrected using the surface image obtained almost simultaneously with the tomographic image.

For example, in the above embodiment, as the low coherence light LO, near-infrared light with a wavelength of about 800 nm to 900 nm is used, but light of longer wavelengths can be used to measure images in the deeper region of the fundus oculi Ef. For example, near-infrared light of a wavelength within about 900 nm to 1000 nm is used, and also near-infrared light of a wavelength within about 1000 nm to 1100 nm can be used.

Moreover, when low coherence light L0 of a wavelength within about 900 nm to 1000 nm is used, the near-infrared light of a wavelength within about 700 nm to 900 nm can be used as the illumination light for the fundus camera unit 1A. Moreover, when the low coherence light LO of a wavelength within about 1000 nm to 1100 nm is used, near-infrared light of a wavelength within about 850 nm to 1000 nm can be used as the illumination light for the fundus camera unit 1A. Herein, in each case, it is desirable to set a longer wavelength for the low coherence light LO than the wavelength of the illumination light of the fundus camera unit 1A, but it is possible to adapt the composition such that the relationship of short and long wavelengths is reversed.

A first image forming part of the fundus observation device related to the present embodiment is not limited to a fundus camera (unit), an arbitrary ophthalmologic device capable of forming a 2-dimensional image of a fundus surface may also be applied. For example, a slit lamp (slit lamp microscopic device) may be used as a first image forming part.

Moreover, in the above embodiment, the forming process of the fundus image by the image forming part 220 (image forming board 208) and each controlling process are operated by the controlling part 210 (microprocessor 201, etc.), but it can be composed to operate these two processes by one or several computers.

Advantages

The fundus observation device related to the present embodiment comprises a first image forming means for forming 2-dimensional images of the surface of the fundus oculi and a second image forming means for forming tomographic images of the fundus oculi. The imaging optical system of the first image forming means forms the imaging optical path. The second image forming means generates the interference light by overlapping the signal light passing through the fundus oculi to the reference light, and forms tomographic images of the fundus oculi based on this interference light.

Optical combination and separation means operates to combine the optical path of the signal light toward the fundus oculi and the imaging optical path. The signal light irradiates onto the fundus oculi through this imaging optical path. Also, optical combination and separation means are used for separating the signal light toward the fundus oculi from the imaging optical path. The separating signal light generates the interference light by overlapping the reference light.

Such optical combination and separation means permits to capture both 2-dimensional images of the surface of the fundus oculi and tomographic images of the fundus oculi. In particular, when the illumination light from the first image forming means irradiates and the illumination from the signal light by the second image forming means irradiate simultaneously, each light through the fundus oculi is separated by the optical path combination and separation means, each light is detected so that the image is formed. Therefore, by the fundus observation device related to the present invention, it is possible to capture both 2-dimensional images of the surface of the fundus oculi and tomographic images of the fundus oculi to be captured simultaneously.

According to the fundus observation device in an aspect of the embodiment, it is possible to prevent alignment indicators from being reflected in the image of the fundus oculi because of: an alignment optical system for projecting an alignment indicator onto the eye, and EL controlling part configured to control the alignment optical system so as to terminate the projection of the alignment indicators onto the eye prior to the detection of the illumination light by the first detection part.

In addition, according to the fundus observation device in an aspect of the embodiment, it is possible to prevent alignment indicators from being reflected in the image of the fundus oculi, while the image is used for correcting the position of the tomographic image of the fundus oculi because of: an alignment optical system for projecting alignment indicators onto the eye, a detection timing controlling part configured to cause the first detection part to detect the illumination light substantially simultaneously with the detection of the interference light by the second detection part, a controlling part configured to control an alignment optical system so as to terminate the projection of the alignment indicators onto the eye prior to the detection by the first detection part, and a correction part configured to correct the image position of the tomographic image of the fundus oculi, which in turn is based on the two-dimensional image of the surface of the fundus oculi.

In addition, for the fundus observation device in an aspect of the embodiment, the detection timing controlling part operates so as to cause the first detection part to detect the illumination light at a certain period prior to and/or after the detection of the interference light by the second detection part, and the controlling part operates so as to cause the alignment optical system to project the alignment indicator onto the eye when the detection by the first detection part is operated during this time prior to and/or after the detection. Therefore, alignment indicators are reflected in the image of the surface of the fundus oculi captured at that certain time prior to and/or after the detection. The examiner can understand the state of the adjustment of the device to the eye (e.g., the state of focus or the state of the position of the device) when capturing a tomographic image by having visual contact with the alignment indicator.

What is claimed is:

1. A fundus observation device comprising:
a first image forming part having an illuminating optical system configured to emit illumination light onto fundus oculi of an eye and an imaging optical system configured to detect the illumination light having reached said fundus oculi by the first detection part, wherein the first image forming part forms a 2-dimensional image of the surface of said fundus oculi based on the detection results by said first detection part;
a second image forming part having a light source configured to emit low coherent light with a wavelength which is different from said illumination light; an interference optical generating part configured to split said emitted low coherent light into the signal light directed towards said fundus oculi and the reference light directed towards a reference object and to generate interference light by superposing the signal light having reached said fundus oculi and the reference light having reached said reference object; and a second detection part configured to detect said interference light generated, wherein said second image forming part forms tomographic images of said fundus oculi based on the detected results by said second detection part;
an optical path combination and separation part configured to combine the photographing optical path formed by said imaging optical system and the optical path of a signal light directed toward said fundus oculi so as to illuminate said signal light onto said fundus oculi through said photographing optical path, and configured to separate said photographing optical path from the optical path of the signal light toward said fundus oculi so as to superpose said signal light on said reference light by said interference optical generating part;

an alignment optical system configured to project an alignment indicator on said eye to preliminarily adjust a device for said eye; and a controlling part configured to control said alignment optical system to terminate projection of said alignment indicator on said eye before said illumination light is detected by said first detection part, wherein said alignment optical system comprises a first alignment optical system which projects a first alignment indicator on said eye for adjusting the focus of said eye, a first alignment light source configured to emit a first alignment light, a split prism configured to split said emitted first alignment light into two light fluxes, and a first optical path-combination part configured to combine said two light fluxes into an optical path toward said fundus oculi, further comprising a drive part configured to detach said first optical path-combination part from said optical path toward the fundus oculi, and said controlling part controls said drive part to evacuate said first optical path-combination part from said optical path toward the fundus oculi, so as to prevent projection of said first alignment indicator on said eye.

2. A fundus observation device according to claim 1, wherein said first alignment optical system comprises a first alignment light source configured to emit a first alignment light, a split prism configured to split said emitted first alignment light into two light fluxes and a first optical path-combination part configured to combine said two light fluxes into an optical path toward said fundus oculi, wherein said controlling part controls said first alignment indicator to be prevented from projection on said eye by turning off said first alignment light source.

3. A fundus observation device according to claim 1, wherein said alignment optical system comprises a second alignment optical system that projects a second alignment indicator on said eye for adjusting the position of the device relative to said eye.

4. A fundus observation device according to claim 1, wherein said second alignment optical system comprises a second alignment light source configured to emit a second alignment light, a light guide configured to guide said emitted second alignment light, a two-hole aperture configured to generate two light fluxes out of said second alignment light emitted from an emission end of said light guide, and a second optical path-combination part configured to combine said two fluxes into the optical path toward the fundus oculi, wherein said controlling part controls said second alignment indicator to be prevented from projection on said eye by turning off said second alignment light source.

* * * * *